United States Patent
Khodakarami et al.

(10) Patent No.: US 11,845,670 B2
(45) Date of Patent: Dec. 19, 2023

(54) TASK-SPECIFIC IONIC LIQUIDS FOR SELECTIVE SEPARATION AND RECOVERY OF RARE EARTH ELEMENTS

(71) Applicant: The Curators of the University of Missouri, Columbia, MO (US)

(72) Inventors: Mostafa Khodakarami, Rolla, MO (US); Lana Alagha, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 17/595,334

(22) PCT Filed: May 15, 2020

(86) PCT No.: PCT/US2020/033053
§ 371 (c)(1),
(2) Date: Nov. 15, 2021

(87) PCT Pub. No.: WO2020/236550
PCT Pub. Date: Nov. 26, 2020

(65) Prior Publication Data
US 2022/0212945 A1 Jul. 7, 2022

Related U.S. Application Data

(60) Provisional application No. 62/849,244, filed on May 17, 2019.

(51) Int. Cl.
| | |
|---|---|
| C01F 17/00 | (2020.01) |
| C01F 17/17 | (2020.01) |
| C22B 3/28 | (2006.01) |
| C07C 211/63 | (2006.01) |
| C07C 229/12 | (2006.01) |
| C07C 235/06 | (2006.01) |
| C22B 59/00 | (2006.01) |

(52) U.S. Cl.
CPC ............ *C01F 17/17* (2020.01); *C07C 211/63* (2013.01); *C07C 229/12* (2013.01); *C07C 235/06* (2013.01); *C22B 3/288* (2021.05); *C22B 59/00* (2013.01)

(58) Field of Classification Search
CPC .... B01D 11/0492; B01D 11/04; B01D 57/00; C01F 17/17; C01F 17/10; C22B 59/00; C22B 3/0016; C22B 3/14; C22B 3/288; C07C 211/63; C07C 229/12; C07C 235/06
See application file for complete search history.

(56) References Cited

FOREIGN PATENT DOCUMENTS

WO 2007147222 A2 12/2007

OTHER PUBLICATIONS

CN 105219979 A, Jan. 6, 2016. (Year: 2016).*
Rout et al., "Solvent Extraction of Neodymium(III) by Functionalized Ionic Liquid Trioctylmethylammonium Dioctyl Diglycolamate in Fluoring-free Ionic Liquick Diluent", I&EC Research, 2014, vol. 53, pp. 6500-6508.
Qiu et al., "Application of a functionalized ionic liquid extractant tributylethylammonium dibutyldiglycolamate ([A336] [BDGA]) in light rare earth extraction and separation", PLOS ONE, Aug. 23, 2018, 13 pages.
International Search Report for PCT/US2020/33053, dated Jul. 28, 2020, 2 pages.

* cited by examiner

*Primary Examiner* — Steven J Bos
(74) *Attorney, Agent, or Firm* — Armstrong Teasdale LLP

(57) ABSTRACT

The present disclosure is directed to novel functionalized ionic liquids (ILs) that are used, for example, for enhanced recovery and separation of rare earth elements from aqueous solutions. The liquids and processes disclosed herein lead to greater separation efficiency, increased stability of separation materials, increased selectivity, and a reduced amount of waste materials.

6 Claims, 27 Drawing Sheets

TASK-SPECIFIC IONIC LIQUIDS FOR SELECTIVE SEPARATION AND RECOVERY OF RARE EARTH ELEMENTS

This application is a National Stage Entry of PCT/US2020/033053, filed May 15, 2020, which claims priority to U.S. Provisional Patent Application Ser. No. 62/849,244, filed on May 17, 2019, the contents of which is are hereby incorporated by reference in its their entireties.

FIELD OF THE DISCLOSURE

Described herein are a novel type of functionalized ionic liquids (ILs) for enhanced recovery and separation of rare earth elements from aqueous solutions. Complexing functionalities are incorporated into both anionic and cationic parts of the ILs. In some embodiments, both the anions and cations of the ionic liquids are composed of only C, H, O, and N atoms, which all are incinerable and therefore reduce the amount of solid wastes. The inner synergistic effect provided by both the cation and the anion helps to improve the loading capacity and kinetics of the extraction process. Incorporating a bi-dentate betaine derivative ligand with two oxygen donating atoms into the cationic component results in decrease of reagent consumption and making the extraction very efficient and fast. Easy synthesis, stability in a wide range of temperature, and very high selectivity are other important advantages of the ionic liquids described herein.

BACKGROUND OF THE DISCLOSURE

Due to their unique magnetic, luminescent, and electrochemical properties, rare earth elements (REEs) have become the foundation of several technologies and have been used extensively in many industries such as modern electronics, green energy, transportation, health care and defense. Rare earth elements and their compounds are further of crucial importance for a large number of rapidly expanding industrial applications such as catalysis, metallurgy, petroleum, electronics and renewable energy. As these industry sectors are growing, the global consumption of rare earth elements is going to increase dramatically.

However, the separation and recovery of rare earth elements and compounds including rare earth elements have been very challenging due to their complex chemistries. Among the different separation and purification techniques, the separation and extraction of rare earth elements heavily relies on solvent extraction, due to several advantages such as suitability over a wide range of operation scales and the relatively simple equipment. However, the existing separation technologies for rare earth elements that primarily use solvent extraction process, suffer from low separation efficiency, poor stability of separation materials, limited selectivity and production of huge amount of waste materials. There is a need, therefore, for development of safer and more efficient processes that rely on the design of green and highly selective extractants.

According to the U.S. department of energy (DOE) criticality matrix, rare earth elements are among the most critical elements in the medium-term (2015-2025). This criticality assessment is based on the increasing demands of key materials and supply-demand mismatches. Interestingly, the demands of different REEs are not uniformly growing. The current global REE demand is estimated to be 141,000 tons of rare earth elements per annum and is expected to be approximately 210,000 tons in the year 2025. Increasing demand for REEs has led to a worldwide interest in the development of novel rare earth separation and recovery techniques.

Separation and recovery of REEs from natural resources is a quite complicated process due to the relative low concentration of these elements and the complex nature of the host rock. Moreover, REEs have similar physiochemical properties, which makes the separation of individual elements very challenging. Froth flotation and chemical dissolution technologies are usually used for REEs primary enrichment and separation. In recent years, separation and recovery of lanthanides have heavily relied on solvent extraction, also known as liquid-liquid extraction, which usually follows acid leaching of rare earth minerals. Over the last six decades, numerous investigations have been made seeking effective extractants for the recovery and separation of rare earth elements. Table 1 shows selected examples of four categories of extractants that are currently used in rare earth extraction. None of the extractants are entirely satisfactory. It has been reported that the production of 1 ton of rare earth oxide in China produces 60,000 m$^3$ of waste gases, 200 m$^3$ wastewater and 1.4 tons of radioactive waste. Furthermore, the types of solvents used in the extraction processes over the last century have generated fears about their hazardous impact on the environment.

TABLE 1

Conventional organic extractants for the separation and recovery of rare earth elements.

| Extractant Class | Type | Example | General Structure |
|---|---|---|---|
| Acid extractants | Phosphoric acids | D2EHPA | 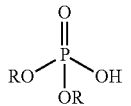 |
|  | Phosphonic acids | PC88A | 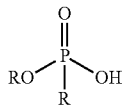 |

TABLE 1-continued

Conventional organic extractants for the separation and recovery of rare earth elements.

| Extractant Class | Type | Example | General Structure |
|---|---|---|---|
| | Phosphonic acids | Cyanex 272 | R-P(=O)(R)-OH |
| | Sulfonic acids | Dinonylnapthalene sulfonic acid | naphthalene-SO$_2$-OH with R groups |
| | Carboxylic acids | Naphthenic acids | ethyl-cyclopentyl-CH$_2$CH$_2$-COOH |
| | | Versatic acids | HO-C(=O)-CR$_2$ |
| Basic extractants | Primary amines | Primene JMT | H$_2$N-C(R$_1$)(R$_2$)(R$_3$) |
| | Secondary amines | N-methylaniline | C$_6$H$_5$-NH-CH$_3$ |
| | Tertiary amines | Alamines | R-N(R)-R |
| | Quaternary amines | Aliquat 336 | R-N$^+$(R)(R)-R, Cl$^-$ |
| Neutral extractants | Phosphorus-based | TBP | RO-P(=O)(OR)-OR |
| | | (TOPO) Cyanex 923 | R-P(=O)(R)-R |
| Chelating extractants | Beta diketones | LIX 54 | alkyl-C(=O)-CH$_2$-C(=O)-phenyl |

The types of solvents used in the extraction processes over the last century have generated fears about their hazardous impact on the environment. Serious attention has been directed towards the development of safer and more efficient commercial processes. Special focus was given to the design of green and highly selective extractants. Recently, ionic liquids, which are molten salts with a melting temperature below 100° C., have gained considerable attention due to their unique physicochemical and structural properties. Among these properties are the low melting point, non-flammability, negligible vapor pressure and most important is the flexibility in structural design that allows to tailor the structure by changing the cationic or anionic component to target a specific metal ion.

ILs have been used in a myriad number of applications as solvents, catalysts and electrolytes in electrochemical devices. Moreover, their unlimited potential of tunability makes them great candidates for selective separation and purification applications. In the field of rare earth recovery, imidazolium, phosphonium, and ammonium based MLs are used as solvents and extractant.

Despite the fact that non-functional ILs have shown higher efficiency in comparison with conventional organic extractants, using non-functional ILs as extractants is scarce due to their non-coordination property where ions interact weakly and less selectively with extractant molecules. Some studies also show that non-functional ILs may not be considered as green and sustainable solvents since they extract metals by ion exchange mechanism and hence release the cationic or anionic components of the ILs into the aqueous phase. Thus, the loss of ILs as a result of ion exchange mechanism will result not only in environmental issues but also in cost increase which is considered as a major barrier for the implementation of ILs at large scale.

The present disclosure addresses the aforementioned challenges through the use of functionalized ILs. Functional ionic liquids are a class of ILs which have task-specific coordination ligands that facilitate the metal extraction by solvation mechanism rather than ion exchange mechanism, thus increasing the life time of the extractant and eliminating the requirement for the costly process of saponification. There is a need, therefore for finding new functional cations and anions with higher binding efficiency and less environmental impact and integrating them into the molecular structure of ionic liquids.

BRIEF DESCRIPTION OF THE DISCLOSURE

In one aspect of the present disclosure, a functionalized ionic liquid is disclosed. The functionalized ionic liquid comprises:
a cationic component and
an anionic component;
wherein the cationic component and the anionic component each individually comprise an oxygen donating group.

In another aspect of the present disclosure, a method of producing a functionalized ionic liquid is disclosed. The method comprises:
forming a first mixture comprising
a compound comprising
a cationic component comprising an oxygen donating group; and
a halogen anionic component;
a base; and
a first solvent;
reacting the first mixture to form a second mixture;
adding to the second mixture a third mixture comprising
a compound comprising a component comprising an oxygen donating group; and
a second solvent; and
reacting the third mixture.

In yet another aspect of the present disclosure, a method of recovering rare earth elements is disclosed. The method comprises:

mixing an aqueous solution comprising a rare earth element with a non-aqueous solution comprising a functionalized ionic liquid, wherein the functionalized ionic liquid comprises a cationic component and an anionic component, and further wherein the cationic component and the anionic component of the functionalized ionic liquid each individually comprise an oxygen donating group;
solvating the rare earth element with the functionalized ionic liquid;
separating a non-aqueous phase comprising the rare earth element from the mixture; and
recovering the rare earth element.

DETAILED DESCRIPTION OF THE DISCLOSURE

Figure 1A:
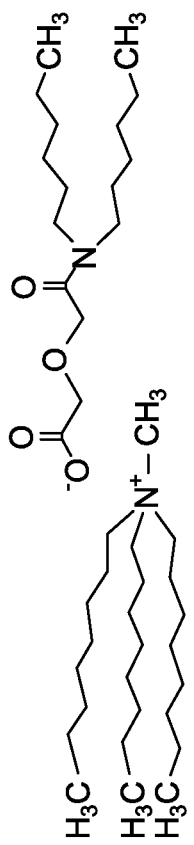
FIG. 1A depicts an exemplary embodiment of a structure of a functionalized ionic liquid in accordance with the present disclosure.

Functionalized ionic liquids according to the present disclosure comprise a cationic component and an anionic component. The cationic component and the anionic component each individually comprise an oxygen donating group.

In some embodiments of the present disclosure, the oxygen donating groups of the cationic component and anionic component have different denticities. In some embodiments of the present disclosure, the oxygen donating groups of the cationic component have a higher denticity than the oxygen donating groups of the anionic component. In some embodiments of the present disclosure, the oxygen donating groups of the cationic component have a lower denticity than the oxygen donating groups of the anionic component.

In some embodiments of the present disclosure, the oxygen donating group of the cationic component is a bidentate ligand. In some embodiments of the present disclosure, the oxygen donating group of the anionic component is a tridentate ligand.

In some embodiments of the present disclosure, the cationic component is selected from the group consisting of tricaprylmethyl ammonium, trioctyl(2-ethoxy-2-oxoethyl) ammonium, tributylmethyl ammonium, tributyl(2-ethoxy-2-oxoethyl)ammonium, and combinations thereof.

In some embodiments of the present disclosure, the anionic component is selected from the group consisting of dihexyl diglycolamate, dioctyl diglycolamate, dibutyl diglycolamate and combinations thereof.

In some embodiments of the present disclosure, the functionalized ionic liquid is selected from the group consisting of trioctyl(2-ethoxy-2-oxoethyl)ammonium dihexyl diglycolamate and tricaprylmethylammonium dihexyl diglycolamate.

In some embodiments of the present disclosure, the ratio of cation to anion in the FILs is from about 0.1:5.0, from about 0.5:2.0; from about 1:1, from about 2.0:0.5, or from about 5.0:0.1, and ratios therebetween.

In some embodiments of the present disclosure, functionalized ionic liquids are produced according to a method comprising forming a first mixture comprising a halogen anionic component and a compound comprising a cationic component comprising an oxygen donating group, a base, and a first solvent; reacting the first mixture to form a second mixture; adding to the second mixture a third mixture comprising a compound comprising a component comprising an oxygen donating group and a second solvent; and reacting the third mixture.

In some embodiments of the present disclosure, the base is selected from the group consisting of sodium hydroxide, potassium hydroxide, and combinations thereof.

In some embodiments of the present disclosure, the first solvent is selected from the group consisting of ethanol, chloroform, and combinations thereof.

In some embodiments of the present disclosure, the second solvent is dichloromethane.

In some embodiments of the present disclosure, the functionalized ionic liquids are used in a method of separating and recovering rare earth elements, the method comprising mixing an aqueous solution comprising a rare earth element with a non-aqueous solution comprising a functionalized ionic liquid, solvating the rare earth element with the functionalized ionic liquid, separating a non-aqueous phase comprising the rare earth element from the mixture, and recovering the rare earth element. The functionalized ionic liquid comprises a cationic component and an anionic component and the cationic component and the anionic component of the functionalized ionic liquid each individually comprise an oxygen donating group.

In some embodiments of the present disclosure, the rare earth element is selected from the group consisting of light rare earth elements, medium rare earth elements, heavy rare earth elements, and combinations thereof.

In some embodiments of the present disclosure, the rare earth element is selected from the group consisting of dysprosium, cerium, praseodymium, neodymium, promethium, samarium, europium, gadolinium, terbium, holmium, erbium, thulium, ytterbium, lutetium, scandium, yttrium, and lanthanum, and combinations thereof.

In some embodiments of the present disclosure, the aqueous solution comprising a rare earth element comprises a rare earth element obtained from a mineral deposit, a waste material, a recycled material, and combinations thereof. In some embodiments of the present disclosure, a concentration of a rare earth element in the aqueous solution comprising a rare earth element is equivalent to a concentration of a rare earth element obtained from a mineral deposit, a waste material, a recycled material, and combinations thereof.

As used herein, the term "rare earth element" refers to at least one of dysprosium (Dy), cerium (Ce), prasedymium (Pr), neodymium (Nd), promethium (Pm), samarium (Sm), europium (Eu), gadolinium (Gd), terbium (Tb), holmium (Ho), erbium (Er), thulium (Tm), ytterbium (Yb), lutetium (Lu), scandium (Sc), yttrium (Y) and lanthanum (La).

Rare earth elements are classified based on the differences in their chemical and physical properties such as atomic number, electron configuration and double-salt solubility. In one classification, REEs are characterized as light, medium, and heavy. The present disclosure covers light, medium and heavy rare earth elements. The light rare earth elements include, for example, Sc, La, Ce, Pr, Nd, and Pm. The medium rare earth elements include, for example, Sm, Eu, and Gd. The heavy rare earth elements include, for example, Y, Tb, Dy, Ho, Er, Tm, Yb, and Lu.

Usually, a mixture of extractants are used to increase the efficiency of solvent extraction. Using two or more extractants, which are expensive chemicals, is costly. But the cost is not the only problem. Optimum efficiency of each extractant is achieved in a specific diluent. Therefore, the selection of proper diluents is a challenge in synergistic solvent extraction. Difficult regeneration of extractants and greater environmental risks are other problems that occur when a mixture of extractants are used. The ionic liquids described herein not only address the aforementioned issues, but also open a new window on designing smarter ionic liquids with double tasks to be used in more complex systems.

Described herein, are, for example, two novel functional ILs (FILs) with oxygen donating groups: trioctyl(2-ethoxy-2-oxoethyl)ammonium dihexyl diglycolamate, [OcGBOEt][DHDGA], and tricaprylmethylanumonium dihexyl diglycolamate, [A336][DHDGA] that were prepared and tested for the recovery and separation of rare earth elements from aqueous solutions. Both anions and cations of ionic liquids are composed of only C, H, O, and N atoms, which are incinerable and therefore would help to reduce the amount of solid wastes produced by the extraction process. In some embodiments, the anionic component of FILs is a novel diglycolamide-based ligand, N,N-dihexyldiglycolamate that is a tridentate ligand which is expected to enhance the extraction efficiency, due to the presence of three oxygen atoms in the ligand structure. Aliquat 336 or [A336], which was used as the cation in [A336][DHDGA], was functionalized by replacing the methyl group with a bidentate betaine derivative with two oxygen donating atoms that was used to prepare [OcGBOEt][DHDGA]. This functionalization of the cationic component resulted in an increase of the loading capacity and acceleration of the extraction kinetics. The synthesized FILs were characterized using nuclear magnetic resonance (NMR), Fourier transform infrared spectroscopy (FTIR), high-resolution mass spectrometry (HRMS), thermal gravimetric analysis (TGA), disc scanning calorimetry (DSC) in addition to density and viscosity analysis.

The extraction behavior of europium ions ($Eu^{3+}$) in $HNO_3$ solution was investigated in detail by changing key process parameters, including solution acidity, concentration of $Eu^{3+}$, temperature, extraction time, and the type of organic diluent. Kinetic studies indicated that the extraction process was relatively fast with 88% of europium ions extracted in 2 minutes and 97% in 5 minutes using [OcGBOEt][DHDGA], while it took 15 minutes for [A336][DHDGA] to reach 80% recovery. Extraction thermodynamics was evaluated by analyzing the effect of temperature on the extractability of europium ions in nitrate solution. Results indicated that the extraction reactions were favorable for both FILs. Back extraction studies indicated that about 99% of $Eu^{3+}$ can be stripped off the [OcGBOEt][DHDGA] and [A336][DHDGA] using 0.1 and 0.5 M $HNO_3$, respectively. Separation efficiencies of rare earth ions, including $La^{3+}$, $Pr^{3+}$, $Nd^{3+}$, $Sm^{3+}$, $Eu^{3+}$, $Tb^{3+}$, $Dy^{3+}$, $Y^{3+}$, $Er^{3+}$, and $Lu^{3+}$ were also investigated to examine the potential of the synthesized FILs for the separation of heavy and light rare earth elements. Results showed that the extractability of [OcGBOEt][DHDGA] is higher than that of [A336][DHDGA]. However, [A336][DHDGA] showed superior selectivity over [OcGBOEt][DHDGA].

A primary advantage described herein is the cationic component. In general, for ionic liquids used in solvent extraction of metals, functionality is incorporated into one of the components (usually the anionic part), and the other component takes the responsibility of providing some physical and chemical properties such as hydrophobicity, hydrophilicity, polarity, etc. In the ionic liquid synthesized herein, the functionality has been incorporated into both the cation and the anion, which makes a fundamental difference. The functional groups on both cation and anion are O-donor ligands with different denticity. Dual functionality provides an inner synergistic effect that not only improves the efficiency of extraction but also changes the complexation behavior.

Examples

Materials and Methods

Dihexylamine, diglycolic anhydride, sodium sulfate anhydride, potassium hydroxide, ethanol, and chloroform were obtained from Fisher Scientific Inc. (USA). Dichloromethane, hexane, methyltricaprylammonium chloride, sodium hydroxide, trioctylamine, ethyl bromoacetate, ethyl acetate, toluene, nitric acid, and ammonium hydroxide were purchased from Sigma Aldrich (USA). All chemicals and solvents were of analytical reagent grade and used without further purification unless otherwise stated.

All rare earth nitrates used in this study were purchased from the Alfa Aesar (USA). Stock solutions of REEs were prepared by dissolving their hydrated nitrates (>99%) in deionized water and the pH of aqueous solution was adjusted using nitric acid and ammonium hydroxide. Benchtop centrifuge (Nüve NF400) and rotary evaporator (Buchi-R124) were used for phase separation. 1H-nuclear magnetic resonance and $^{13}$C-nuclear magnetic resonance (NMR) spectra of the synthesized ionic liquids were obtained in deuterated chloroform using a Bruker BioSpin GmbH NMR spectrometer, operating at 399.79 MHz for proton and 100.54 MHz for carbon. Proton and carbon chemical shifts were reported relative to tetramethylsilane (TMS). Further investigations on the structures of FILs were performed using Fourier transform infrared spectroscopy (FTIR) and high-resolution mass spectrometry (Thermo Scientific LTQ Orbitrap XL mass spectrometer, HRMS). The thermal stability of FILs was investigated using thermogravimetric analyzer (TA Instruments Inc., STD Q600) while the phase transition was studied using disc scanning calorimetry (TA Instruments Inc., DSC2010). The density of FILs was measured using a specific gravity bottle (Wilmad LabGlass scientific glassware), and the viscosity was studied by a Haake Mars rheometer. An inductively coupled plasma-atomic emission spectrometer (Avio 200 ICP-AES) was used to determine the concentrations of REEs in the aqueous phase (1% $HNO_3$ solution was used as a wash solution in ICP analysis). For method validation first standards, samples, duplicate sample, spike sample and QC were run. 10 ppm and 1 ppm QC were passed and the spike recovery was 99.76%.

Extraction Tests

Extraction experiments were performed by mixing equal volumes of functionalized ILs (diluted in chloroform) and aqueous solutions of rare earth elements. The phase separation was carried out using a separatory funnel. The aqueous phase was further diluted for ICP analysis if necessary. In the stripping experiments, 2 ml of loaded organic phase was mixed with 2 ml $HNO_3$ solutions of different concentrations, followed by stirring for 75 min to reach equilibrium. The extraction efficiency (% E), distribution ratio (D) stripping percentage (S) and separation factors (SF) were used as performance indicators and were obtained using the following equations:

$$\%E = \left(1 - \frac{C_a}{C_t}\right) \times 100\% \quad (1)$$

$$D = \left(\frac{E}{100-E}\right) \times \frac{V_w}{V_o} \quad (2)$$

$$D = \left(\frac{C_{aq}}{C_{org}}\right) \times 100\% \quad (3)$$

$$SF = \left(\frac{D_1}{D_2}\right) \quad (4)$$

where $C_t$ and $C_a$ are the initial and equilibrium concentrations of rare earth ions in aqueous phase, respectively; $V_w$ and $V_o$ are the volumes of aqueous and organic phases, respectively; $C_{aq}$ is the equilibrium concentration of rare earth ions in stripping acid and $C_{org}$ is the initial concentration of rare earth ions in organic phase. The concentration of rare earth ions was measured in aqueous phase using ICP-AES. All determinations were performed in duplicate to get the average and the relative error as low as possible.

Synthesis and Characterization of Functionalized Ionic Liquids (FILs)

Figure 1B:
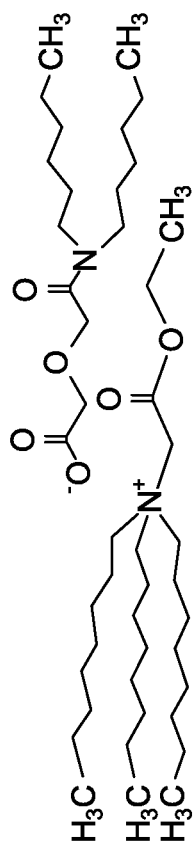
FIG. 1B depicts an exemplary embodiment of a structure of a functionalized ionic liquid in accordance with the present disclosure.

Two types of functionalized ionic liquids were synthesized through alkylation, neutralization, and metathesis reactions. The synthesized FILs were characterized using nuclear magnetic resonance (NMR), Fourier transform infrared spectroscopy (FTIR), high-resolution mass spectrometry (HRMS), thermal gravimetric analysis (TGA), disc scanning calorimetry (DSC) in addition to density and viscosity analysis. The structures of the synthesized FILs used in this exemplary study are shown in FIGS. 1A and 1B. Below are the details about the synthesis and characterization.

Preparation of Dihexyldiglycolamic Acid [DHDGAA]

Figure 15A:
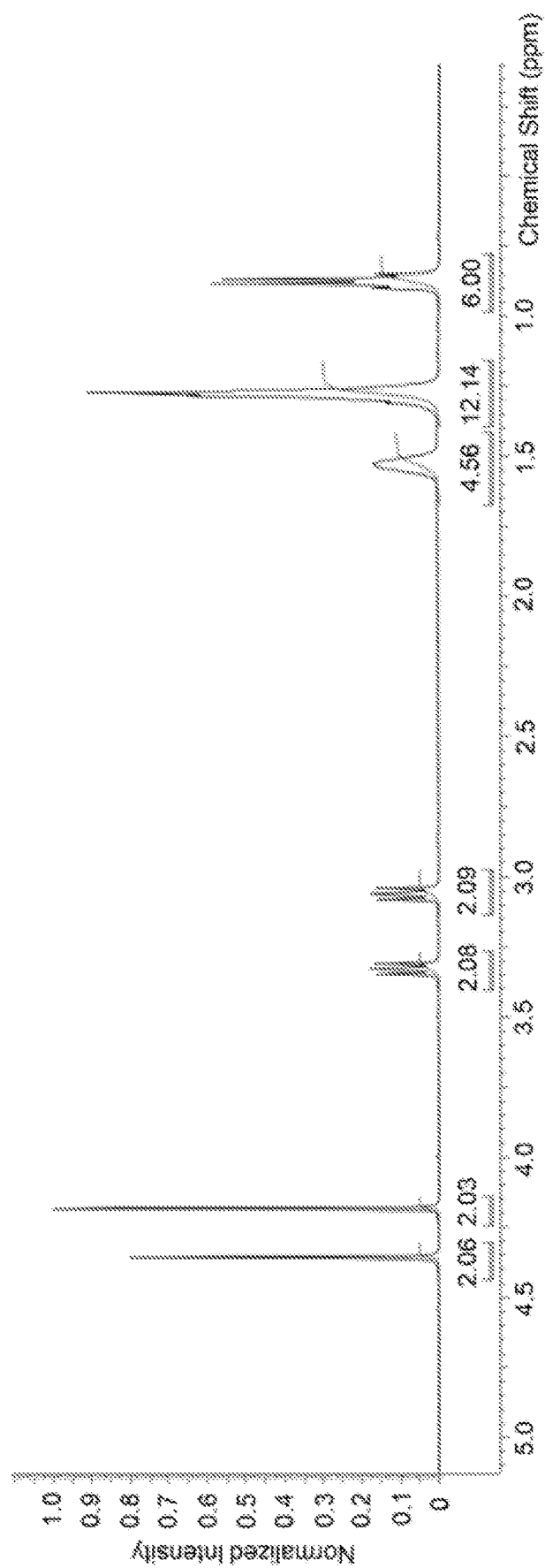
FIG. 15A depicts an exemplary embodiment of $^1$H NMR spectra of DHDGAA in accordance with the present disclosure.
Figure 15B:
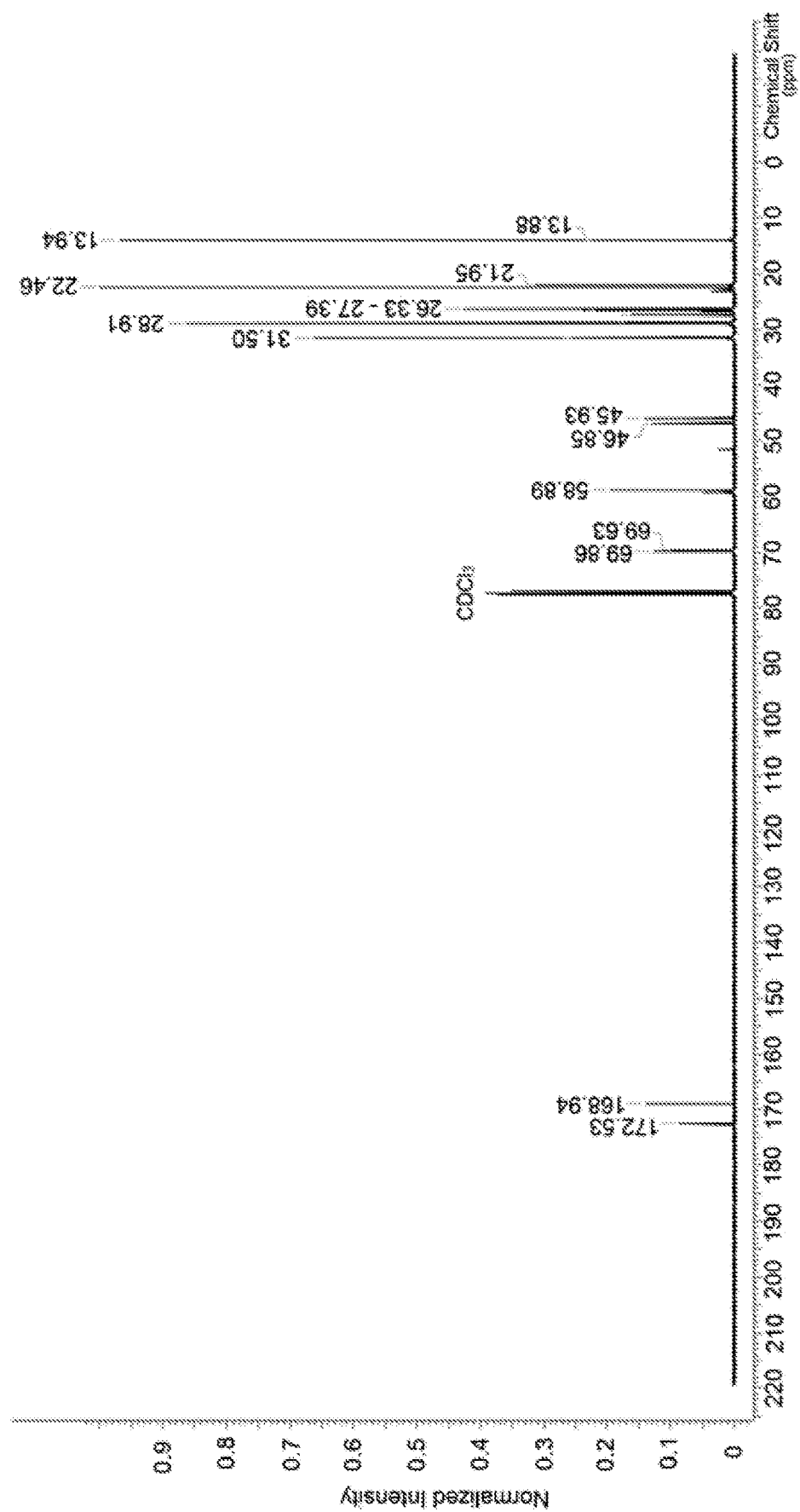
FIG. 15B depicts an exemplary embodiment of $^{13}$C NMR spectra of DHDGAA in accordance with the present disclosure.
Figure 18:
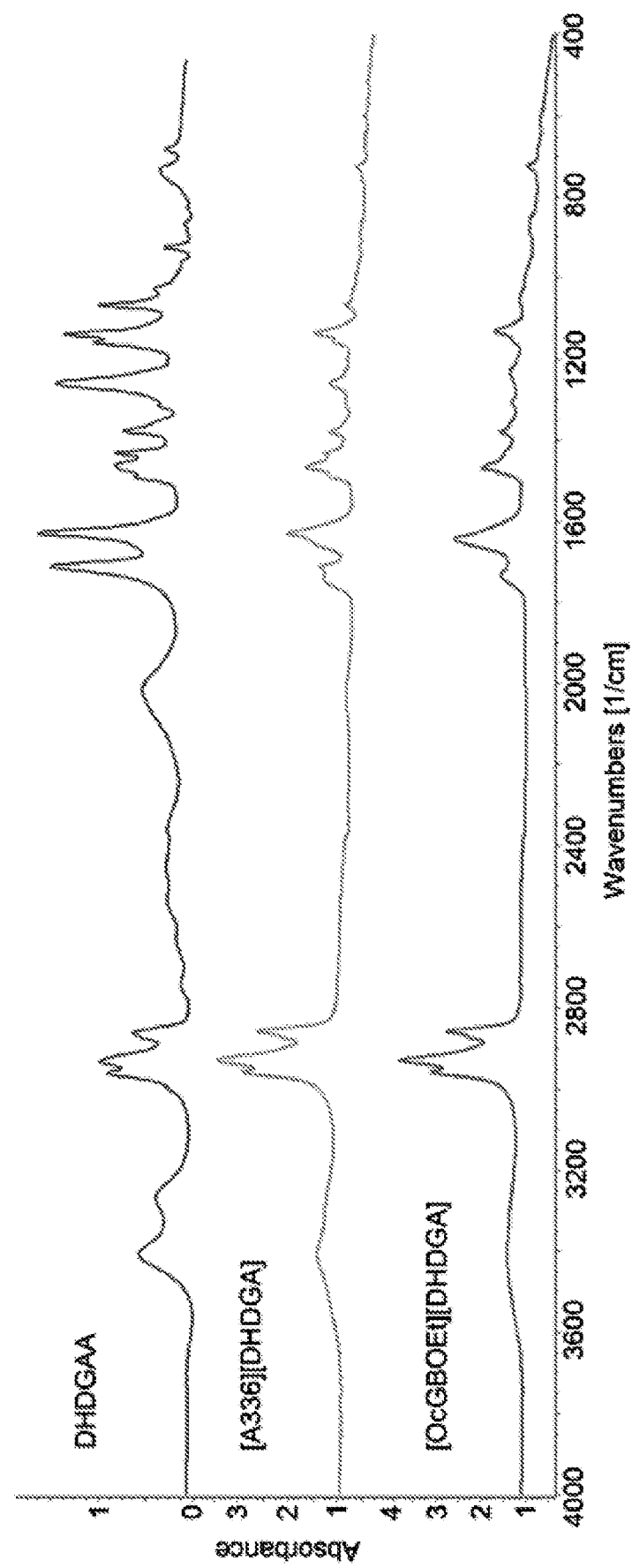
FIG. 18 depicts an exemplary embodiment of FTIR spectra of DHDGAA, [A336][DHDGA], and [OcGBOEt][DHDGA] in accordance with the present disclosure.

Dihexylamine (40 mmol, 7.4 g) was dissolved in 10 mL of dichloromethane and added dropwise in an ice-bath to diglycolic anhydride (40 mmol, 5.8 g) dispersed in 40 mL of dichloromethane. The ice both was then removed, and the reaction was allowed to continue at room temperature for 20 hours. The resulting solution was then washed four times with deionized water and the organic layer was decanted and dried with anhydrous sodium sulfate. The solvent was evaporated under vacuum, and the residue was recrystallized from hexane as a white powder (≈83% yield). The structure was identified by Fourier transform infrared (FTIR), $^1$H and $^{13}$C NMR spectroscopies (see FIGS. 15A-B and 18). IR (cm−1): 3409 (OH), 2960-2862 (CH2), 1712, 1628 (C=O), 1460 (—CH2-CO), 1258 (C—N), 1063 (C—O ether linkage). 1H NMR (400 MHz, CDCl3, δ ppm): 0.67-0.98 (m, 6H), 1.12-1.41 (m, 12H), 1.41-1.70 (m, 5H), 2.94-3.18 (m, 2H), 3.20-3.52 (m, 2H), 3.99-4.26 (m, 2H), 4.28-4.55 (m, 2H). 13C NMR (101 MHz, CDCl3, δ ppm): 13.88, 13.94 (—CH3 groups), 21.95, 22.46, 26.33, 27.39, 28.91, 31.5 (various —CH2— groups), 45.93, 46.85 (CH2-N groups), 69.63 (—CH2O—), 69.86 (—OCH2—), 168.94 (—CON), 172.53 (COOH).

Preparation of Tricaprylmethylammonium Dihexyldiglycolamate. [A336][DHDGA]

Figure 16A:
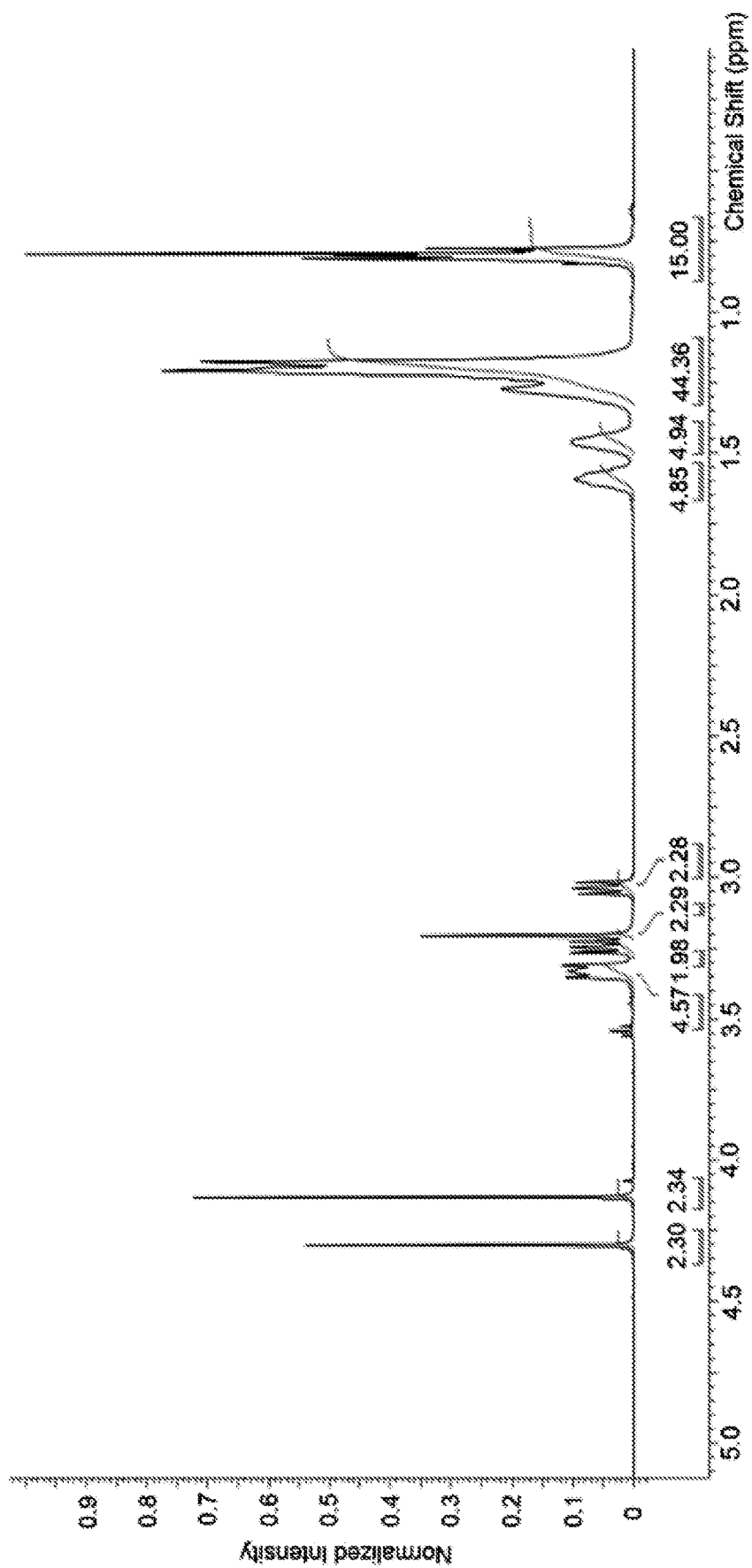
FIG. 16A depicts an exemplary embodiment of $^1$H NMR spectra of [A336][DHDGA] in accordance with the present disclosure.
Figure 16B:
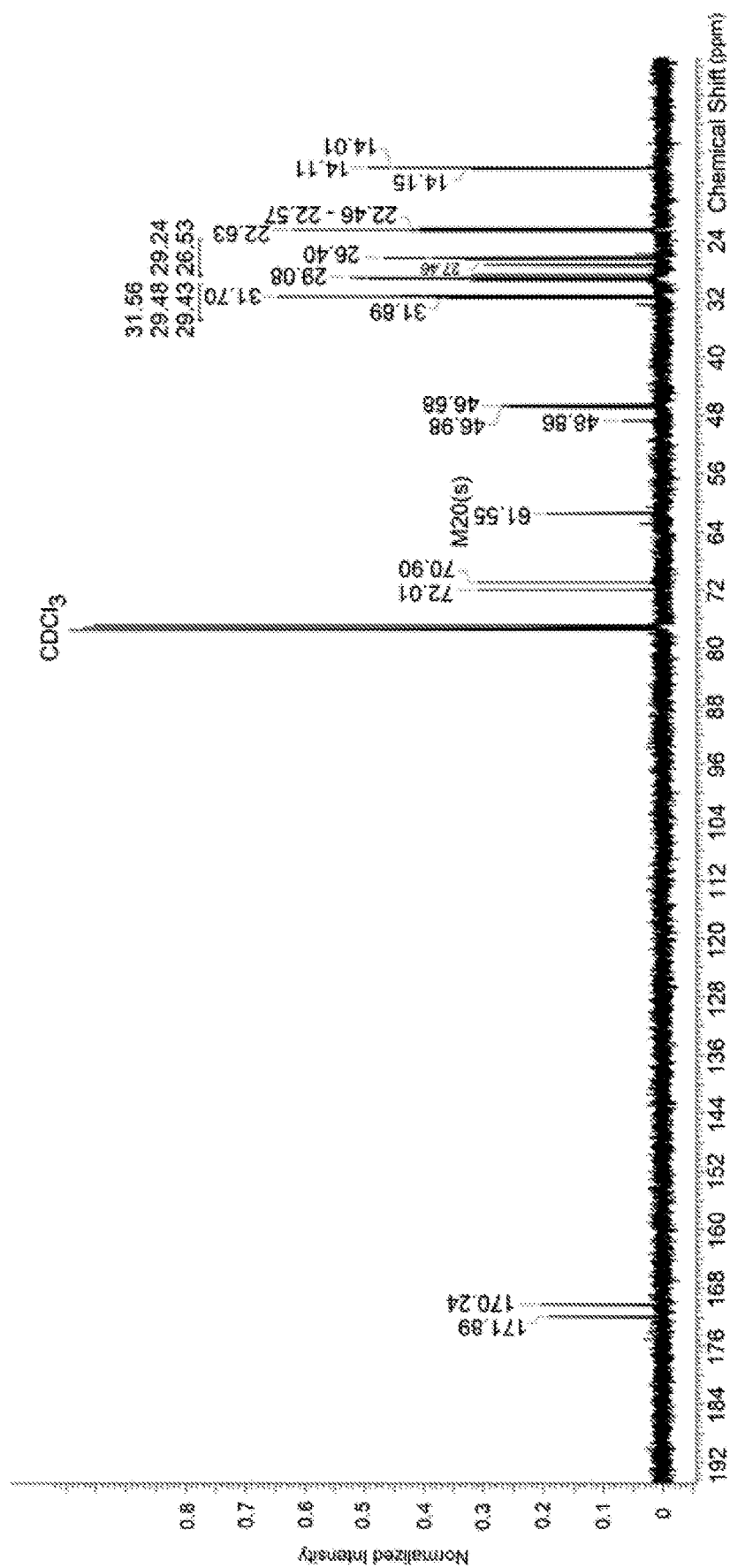
FIG. 16B depicts an exemplary embodiment of $^{13}$C NMR spectra of [A336][DHDGA] in accordance with the present disclosure.

To prepare the tricaprylmethylammonium hydroxide, [A336][OH], 20 mmol (8.1 g) of tricaprylmethylammonium chloride was dissolved in 30 mL of chloroform and then reacted with 20 mL of 4M sodium hydroxide solution made in deionized water. The reaction was carried out for approximately one hour, and then the organic phase was decanted and equilibrated with a fresh 4M NaOH solution. This procedure was repeated eight times and the chloride content was tested with an acidified silver nitrate solution to assure that the chloride content is negligible. The resulting organic layer was washed with deionized water, and the solvent was evaporated under vacuum to yield a viscous [A336][OH] liquid. The [A336][OH] and DHDGAA were then dissolved in dichloromethane (molar ratio 1:1) and refluxed for 12 h. The solvent was rotary evaporated followed by drying at 70° C. in vacuum oven for 7-8 h to yield the yellowish viscous [A336][DHDGA] (≈90% yield). The structure was identified by Fourier transform-infrared (FT-IR), 1H and 13C NMR spectroscopies (see FIGS. 16A-B and 18). IR (cm−1): 2957-2856 (CH2), 1709, 1625 (C=O), 1465 (—CH2-CO), 1258 (C—N), 1063 (C—O ether linkage). $^1$H NMR (400 MHz, CDCl3, δ ppm): 0.67-0.89 (m, 15H), 1.09-1.33 (m, 44H), 1.39-1.51 (m, 5H), 1.54-1.67 (m, 5H), 2.97-3.09 (m, 2H), 3.18-3.22 (m, 2H), 3.23-3.29 (m, 2H), 3.31-3.43 (m, 5H), 4.07-4.18 (m, 2H), 4.25-4.37 (m, 2H). 13C NMR (101 MHz, CDCl3, δ ppm): 14.01, 14.11 (—CH3 groups), 22.46, 22.57, 22.63, 26.53, 26.4, 27.46, 29.08, 29.24, 29.43, 29.48, 31.56, 31.7, 31.89 (various —CH2— groups), 46.68 (CH3N), 46.98 (2×CH2N of [DHDGA]—), 61.55 (3×CH2N of [A336]+), 70.9 (—CH2O—), 72.01 (—OCH2—), 170.24 (—CON), 171.89 (—COO—).

Preparation of trioctyl[2-ethoxy-2-oxoethyl]ammonium Dihexyldiglycolamate, [OcGBOEt][DHDGA]

Figure 17A:
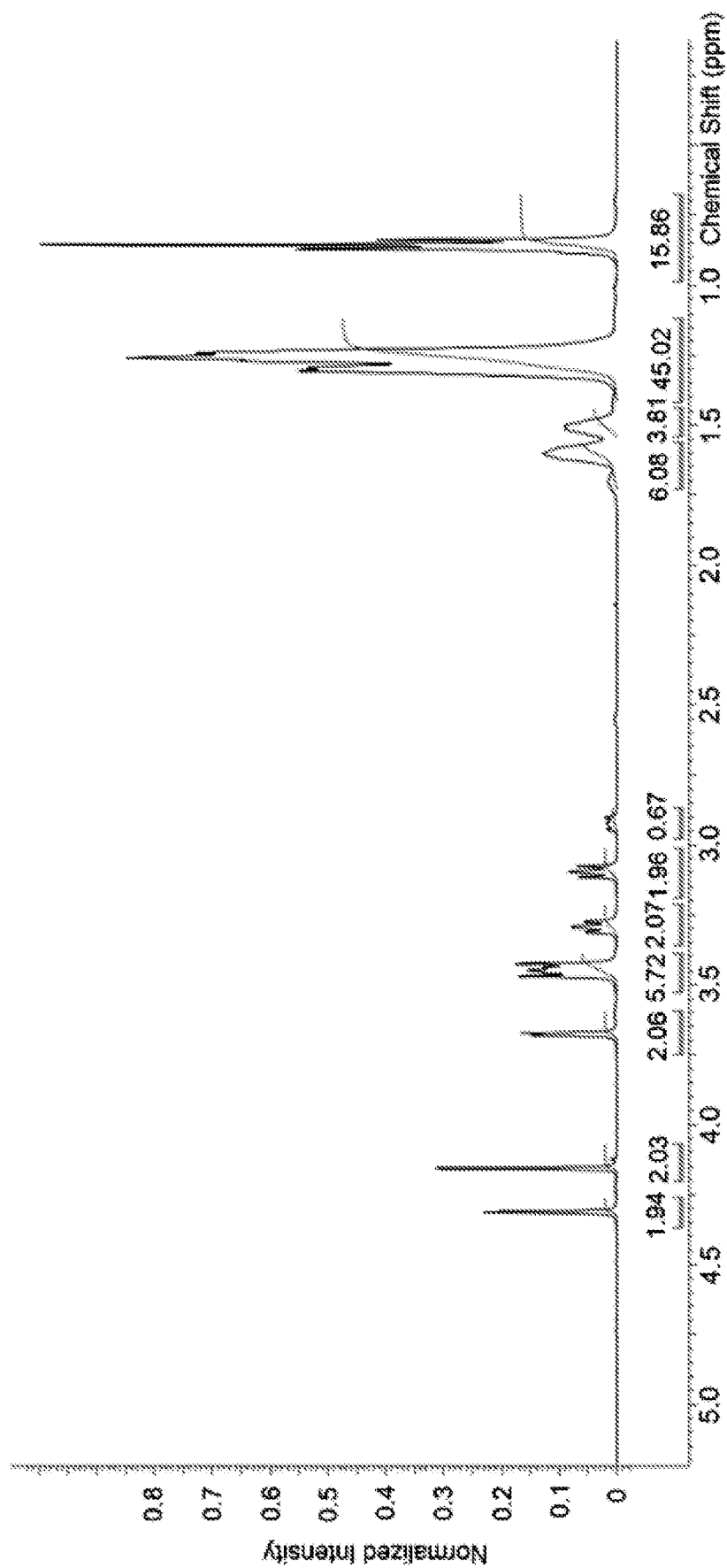
FIG. 17A depicts an exemplary embodiment of $^1$H NMR spectra of [OcGBOEt][DHDGA] in accordance with the present disclosure.
Figure 17B:
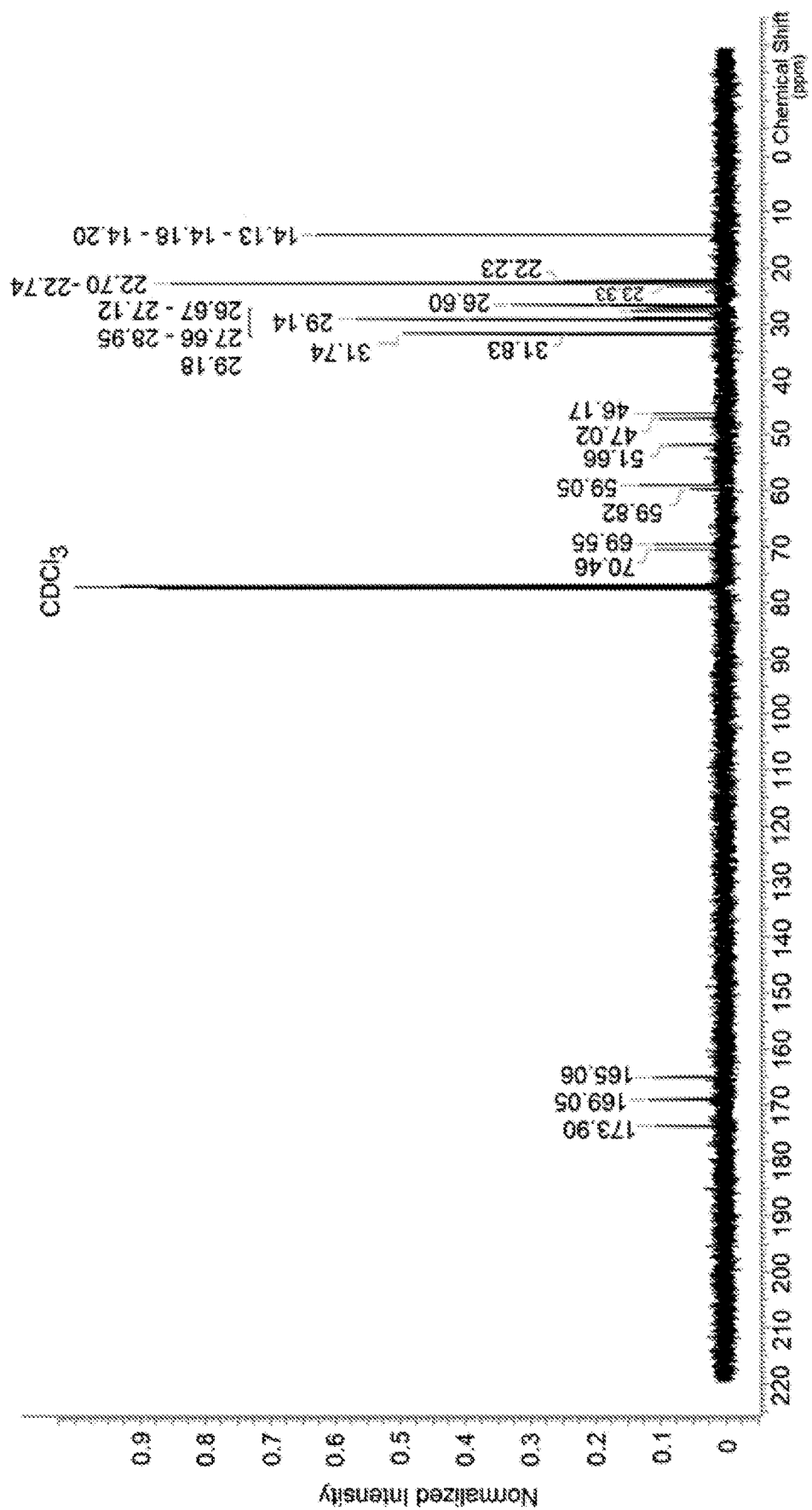
FIG. 17B depicts an exemplary embodiment of $^{13}$C NMR spectra of [OcGBOEt][DHDGA] in accordance with the present disclosure.

Trioctylamine (25.5 mmol, 9 g) was dissolved in ethyl acetate (50 mL), and added dropwise to bromoacetic acid ethyl ester (20 mmol, 3.3 g) in an ice-bath. The mixture was stirred at room temperature for 24 h. The solution was then evaporated under vacuum to give a clear greenish trioctyl (2-ethoxy-2-oxoethyl)ammonium bromide, [OcGBOEt][Br]. 5.8 mmol (3 g) of [OcGBOEt][Br] was dissolved in ethanol (15 mL), and then reacted with 6.9 mmol (3.9 g) of potassium hydroxide dissolved in 25 mL of ethanol. The mixture was stirred for 24 h followed by solid-liquid separation by centrifugation. The ethanol was evaporated thereafter under vacuum, and the [OcGBOEt][OH] was obtained as the intermediate product (97% yield). The subsequent step involved dissolving [OcGBOEt][OH] and DHDGAA in dichloromethane (molar ratio 1:1) and refluxing for 18 h. The solvent was then removed under vacuum and the final product was completely dried at 70° C. using a vacuum oven for about 7-8 h. The final product, [OcGBOEt][DHDGA], was obtained with a yield of 93.13%. The structure was identified by Fourier transform-infrared (FT-IR), 1H and 13C NMR spectroscopies (see FIGS. 17A-B and 18). IR (cm−1): 2957-2856 (CH2), 1734, 1644 (C=O), 1468 (—CH2-CO), 1378 (C—N), 1129 (C—O linkages). 1H NMR (400 MHz, CDCl3, δ ppm): 0.67-0.99 (m, 16H), 1.12-1.42 (m, 45H), 1.44-1.54 (m, 4H), 1.56-1.73 (m, 6H), 2.87-2.98 (m, 1H), 3.01-3.19 (m, 2H), 3.21-3.36 (m, 2H), 3.39-3.53 (m, 6H), 3.59-3.75 (m, 2H), 4.07-4.20 (m, 2H), 4.26-4.37 (m, 2H). 13C NMR (101 MHz, CDCl3, δ ppm): 14.13, 14.18, 14.20 (—CH3 groups), 22.23, 22.70, 22.74, 23.33, 26.60, 26.67, 27.12, 27.66, 28.95, 29.14, 29.18, 31.74, 31.83 (various —CH2— groups), 46.17 (CH3N), 47.02 (2×CH2N of [DHDGA]−), 51.66, 59.05 (2×CH2 of betaine in [OcGBOEt]+), 59.82 (3×CH2N of [OcGBOEt]+), 69.55 (—CH2O— of [DHDGA]−), 70.46 (—OCH2— of [DHDGA]−), 165.06 (—COO— of [OcGBOEt]+), 169.05 (—CON), 173.90 (—COO— of [DHDGA]−).

Characterization of Functional Ionic Liquids

High Resolution Mass Spectrometry

Figure 19:
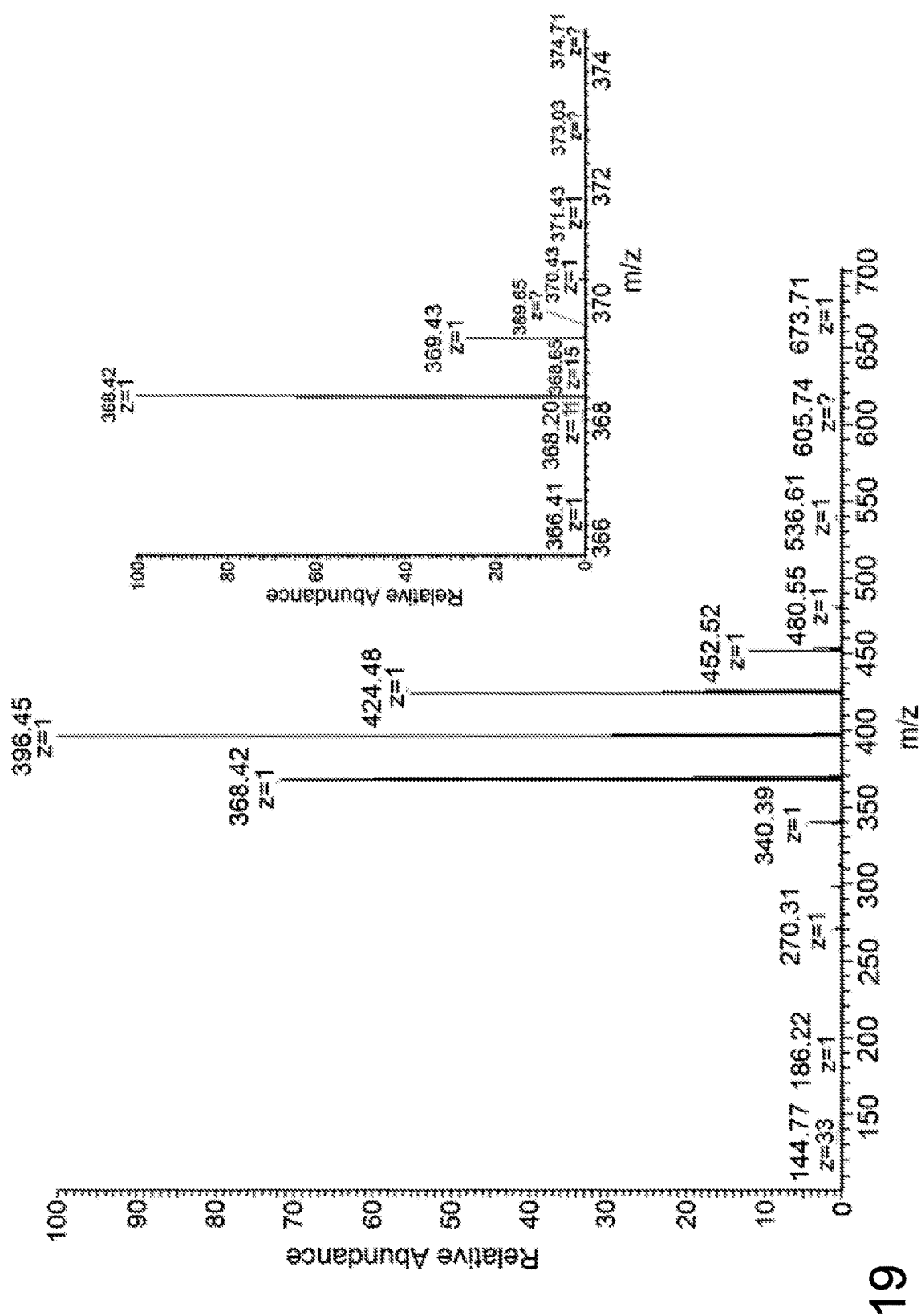
FIG. 19 depicts an exemplary embodiment of an ESI-MS spectrum of [A336][DHDGA] (100-700 m/z) in accordance with the present disclosure.
Figure 20:
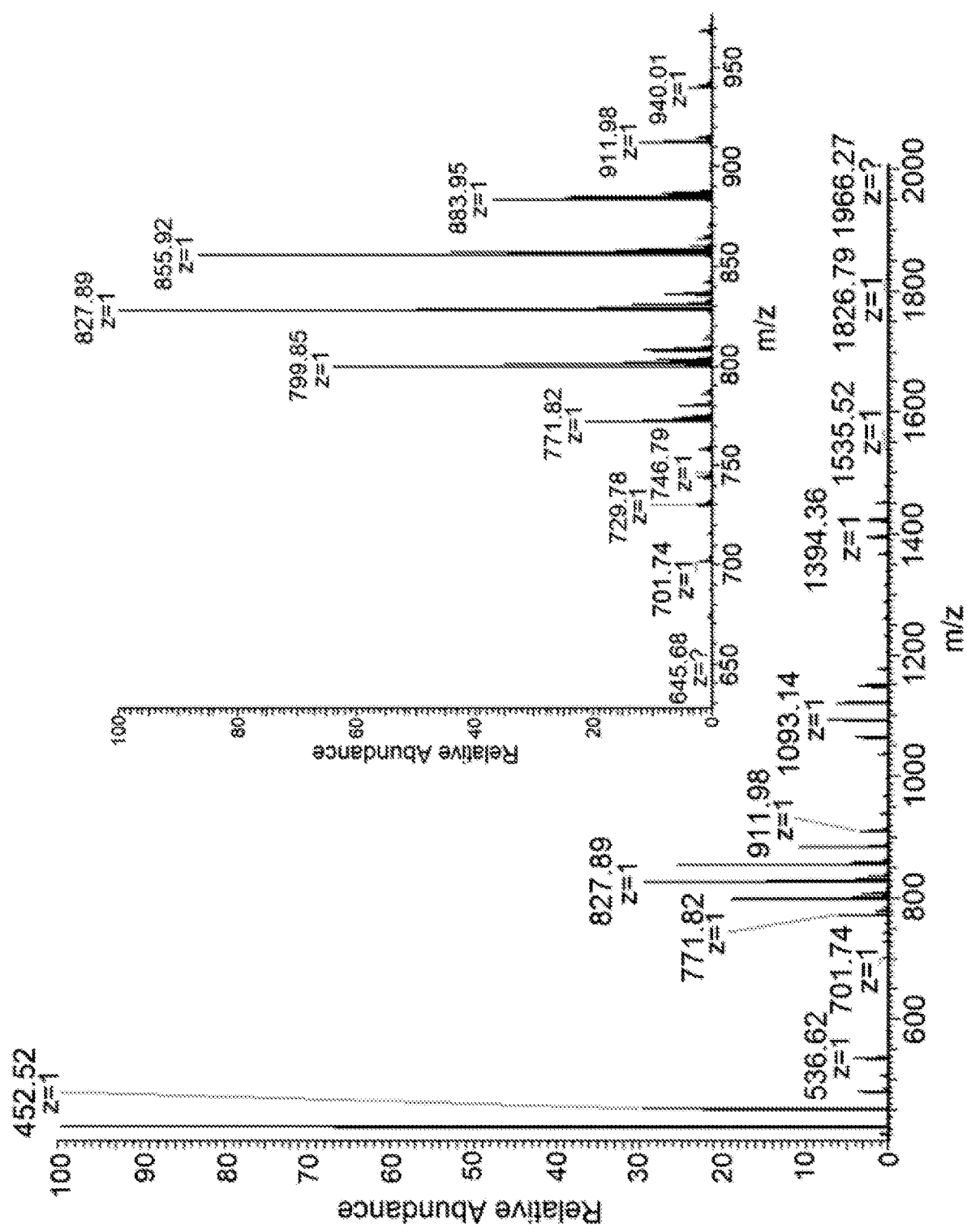
FIG. 20 depicts an exemplary embodiment of an ESI-MS spectrum of [A336][DHDGA] (400-2000 m/z) in accordance with the present disclosure.
Figure 21:
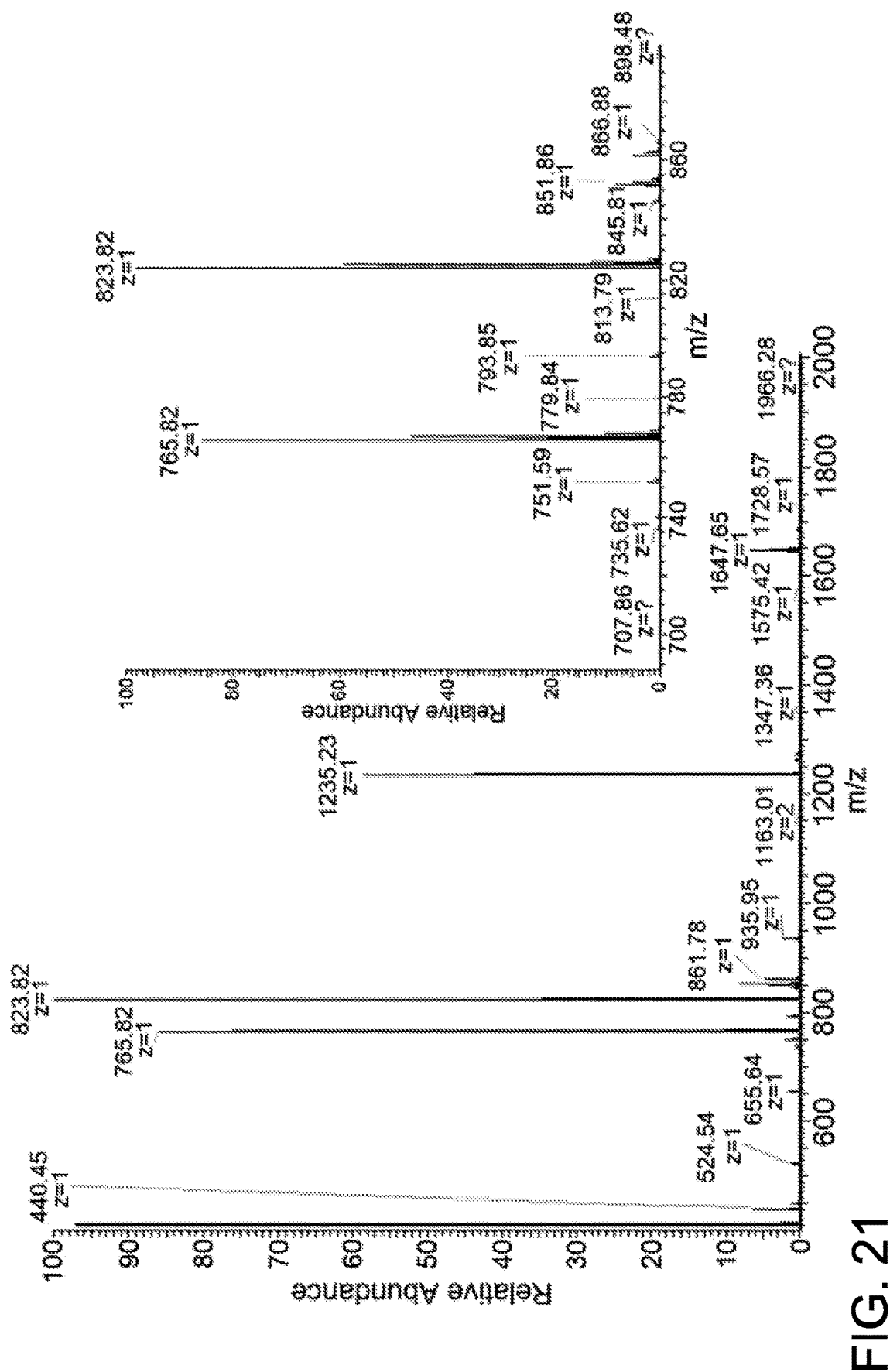
FIG. 21 depicts an exemplary embodiment of an ESI-MS spectrum of [OcGBOEt][DHDGA] (400-2000 m/z) in accordance with the present disclosure.

In addition to FTIR and NMR analysis, a high-resolution mass spectrometry (HRMS) was employed for structural characterization of the compounds. The ionic liquids were diluted (1:100) in acidified acetonitrile (99.9% ACN, 0.1% v/v formic acid) and loaded into a static nanospray ECONO 12 tip (Proxeon) and analyzed by nano-electrospray ionization in positive-ion mode on a Thermo Scientific LTQ Orbitrap XL mass spectrometer. Fourier transform MS data were collected in the Orbitrap (60,000 resolving power, 100-2000 m/z for [A336][DHDGA] and 400-2000 m/z for [OcGBOEt][DHDGA], 1 microscan, maximum inject time of 100 ms, AGC=5e5) over 1 min of direct infusion. The cations of both ionic liquids and different combination of clusters were observed in the HRMS spectrums. In the case of [OcGBOEt][DHDGA], the cationic component was evident at m/z 440.4, and the ionic liquid was observed at m/z 765.8 with a possible Na or K adduct. The analysis of [A336][DHDGA] revealed that the [A336] cation consisted of a mixture of C8 to C10 alkyl chains. According to the HRMS spectrums, dioctyldecylmethyl ammonium (m/z=396.4) and trioctylmethyl ammonium (m/z=368.4) were the predominating components of [A336]+ (see FIGS. 19, 20, and 21).

Thermal Analysis

Figure 22A:
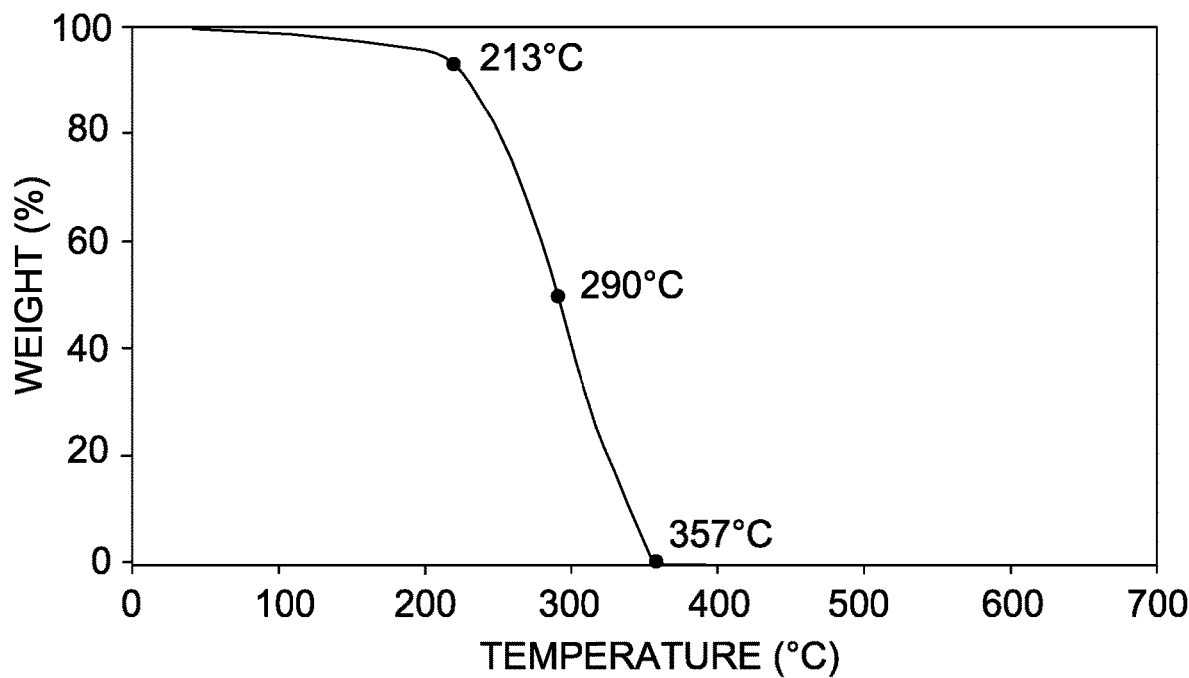
FIG. 22A depicts an exemplary embodiment of a TGA graph for [A336][DHDGA] in accordance with the present disclosure.
Figure 22B:
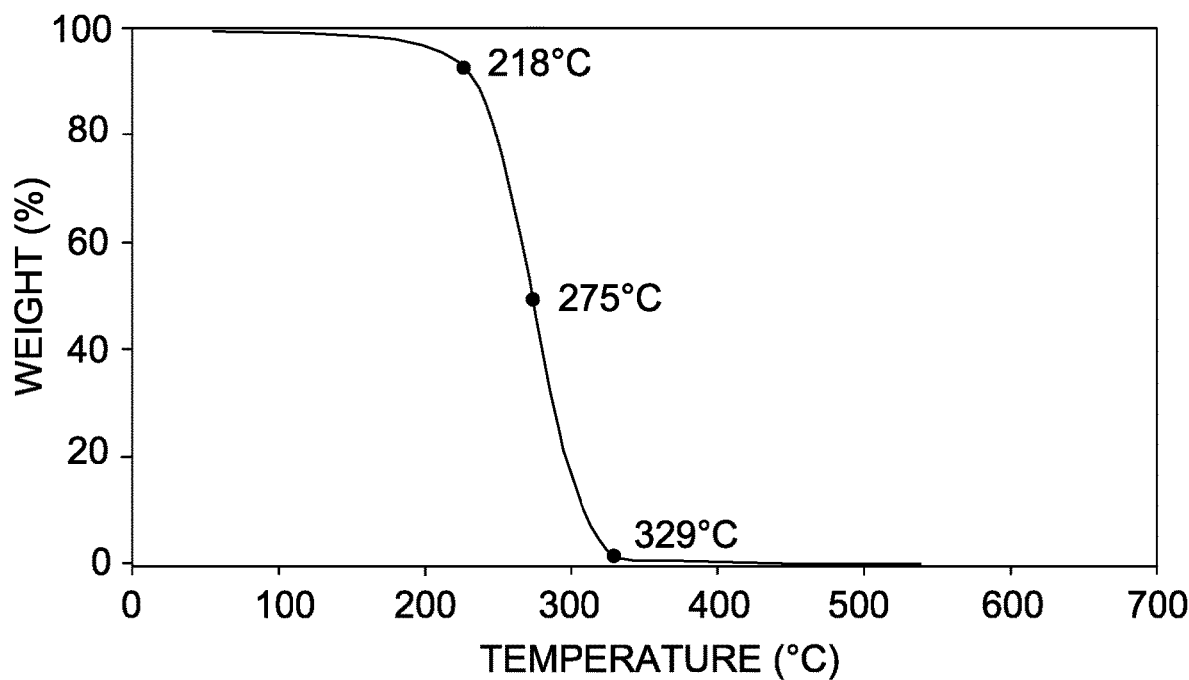
FIG. 22B depicts an exemplary embodiment of a TGA graph for [OcGBOEt][DHDGA] in accordance with the present disclosure.

The thermal stability of functionalized ionic liquids was investigated using a thermogravimetric analyzer (TA Instruments Inc., STD Q600). The samples were heated under nitrogen gas from 20 to 700° C. with a heating rate of 10° C./min. Thermogravimetric analysis (TGA) show that both ionic liquids undergo one step decomposition behavior. The onset decomposition temperatures of [A336][DHDGYA] and [OcGBOEt][DHDGA] were 213 and 218° C., respectively. Two different transitions were observed for both of ionic liquids probably due to the decomposition of different components of ionic liquids at various temperatures. The TGA thermograms showed that the decomposition of [OcGBOEt][DHDGA] is faster than that of [A336][DHDGA]. Results indicated that the [OcGBOEt][DHDGA] fully decomposed at 330° C. while the complete decomposition of [A336][DHDGA] occurred at 356° C. (see FIGS. 22A-B).

Figure 23A:
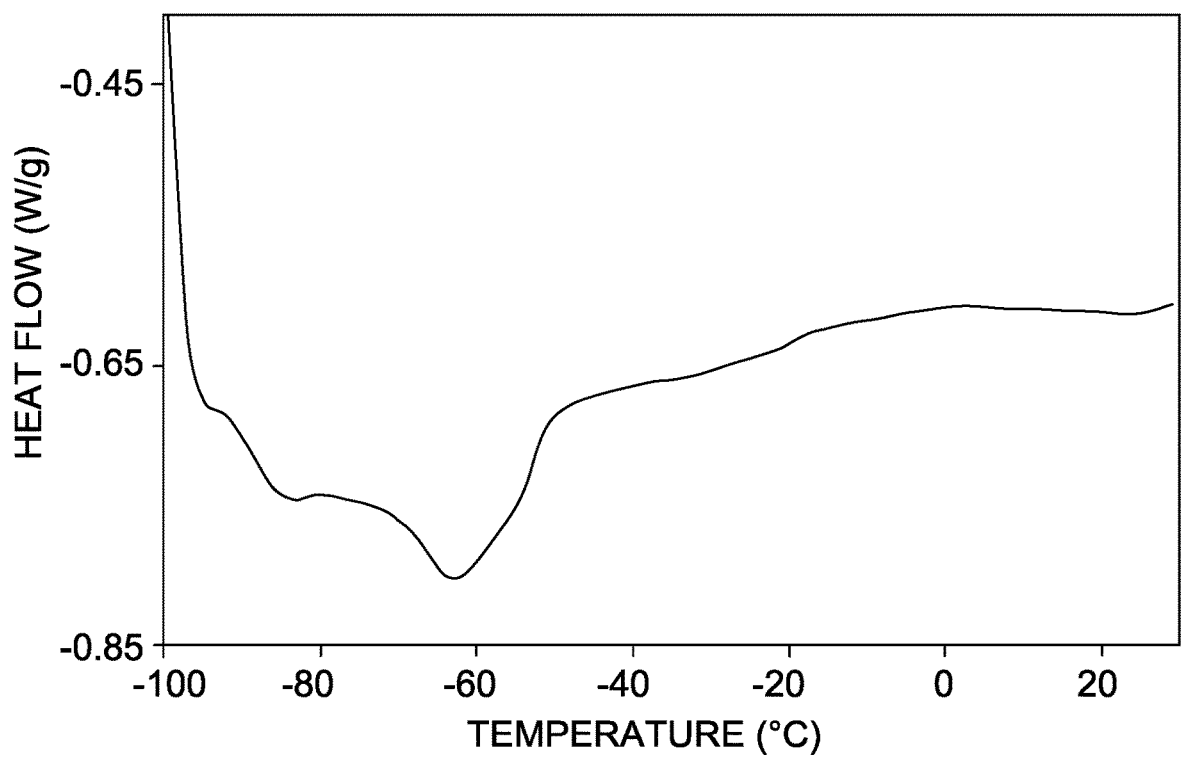
FIG. 23A depicts an exemplary embodiment of a DSC curve for [A336][DHDGA] in accordance with the present disclosure.
Figure 23B:
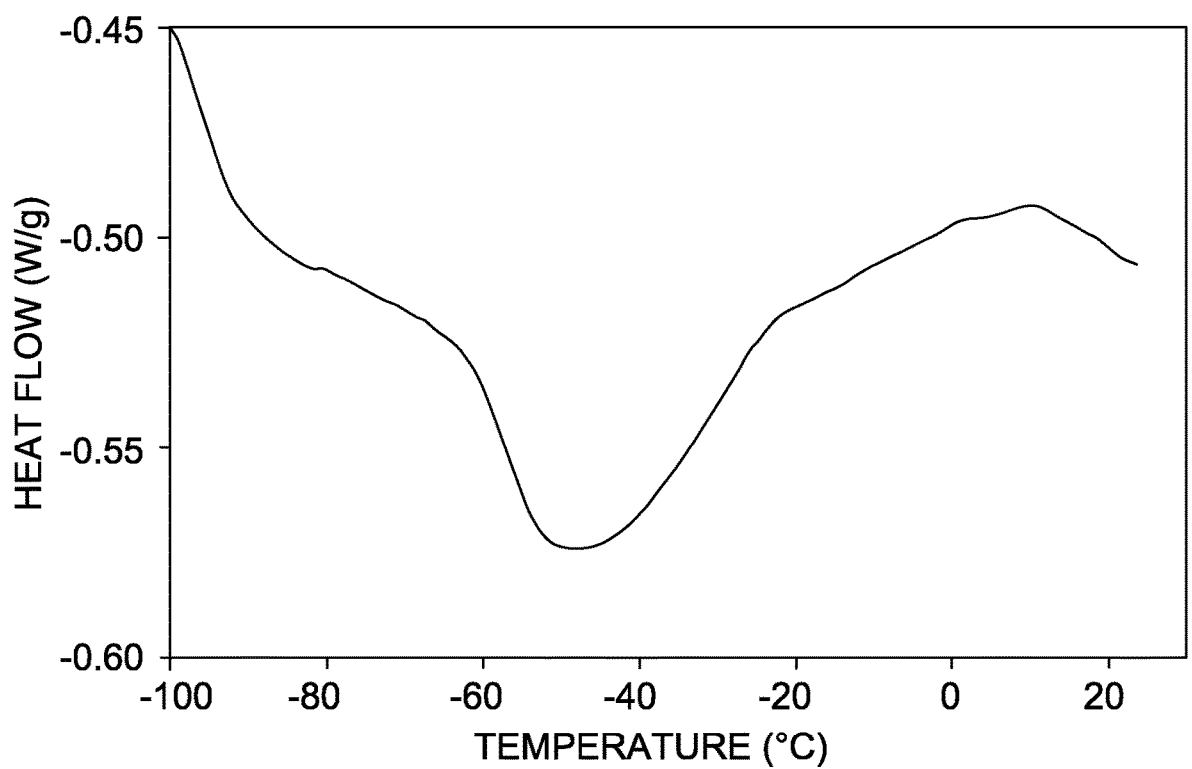
FIG. 23B depicts an exemplary embodiment of a DSC curve for [OcGBOEt][DHDGA] in accordance with the present disclosure.

The solid-liquid phase transition was studied by a differential scanning calorimeter (TA Instruments Inc., DSC2010) with a heating rate of 10° C.% min. The analysis was done under a nitrogen atmosphere in the temperature range of −100 to 30° C. DSC analysis showed that both ionic liquids present a very weak tendency to crystallize. The glass transition temperatures of [A336][DHDGA] and [OcGBOEt][DHDGA] were found to be −63° C. and −56° C., respectively. This demonstrates that the [OcGBOEt][DHDGA] ions need more energy to move around as compared to [A336][DHDGA] ions (see FIGS. 23A-B).

Viscosity and Density Measurement

Densities of ionic liquids were measured at room temperature by weighing in a standard 2 mL specific gravity bottle. The density of [A336][DHDGA] was determined to be 1.19 g/mL, slightly larger than the density of [OcGBOEt][DHDGA] which had a density of 1.14 g/mL. Functionalization of [A336]+ increased both the mass and volume of ionic liquid, however, the density measurement demonstrated that the increase in volume has larger contribution to the density of [OcGBOEt][DHDGA].

Figure 24A:
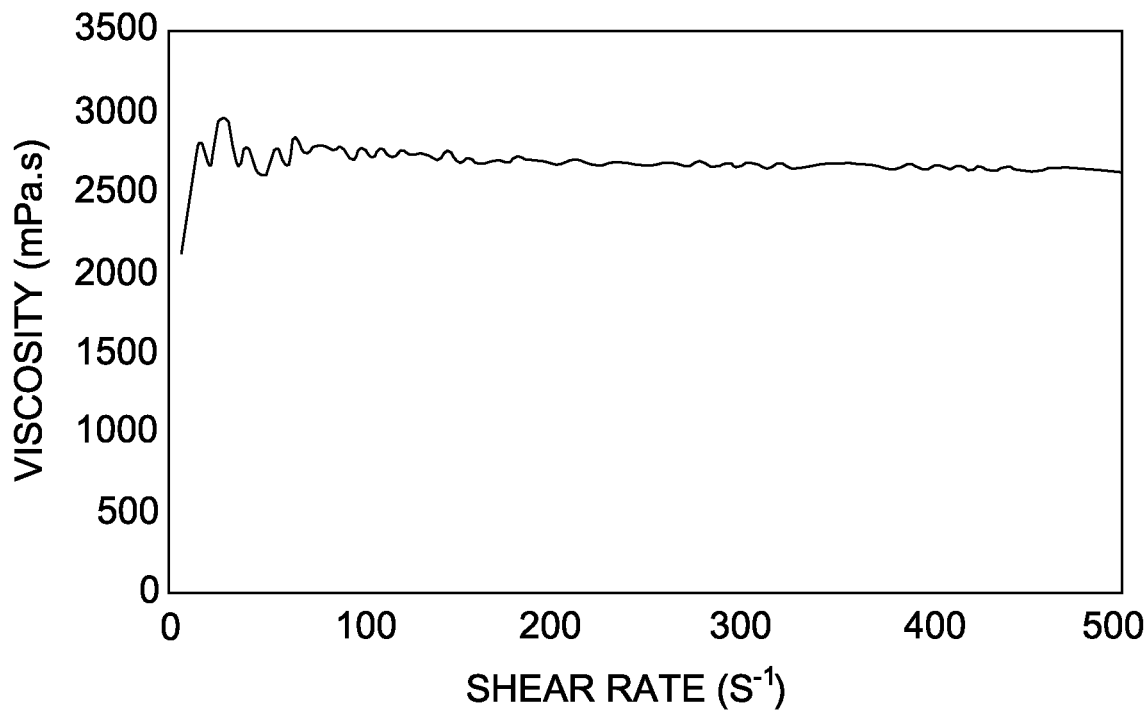
FIG. 24A depicts an exemplary embodiment of a viscosity curve for [A336][DHDGA] in accordance with the present disclosure.
Figure 24B:
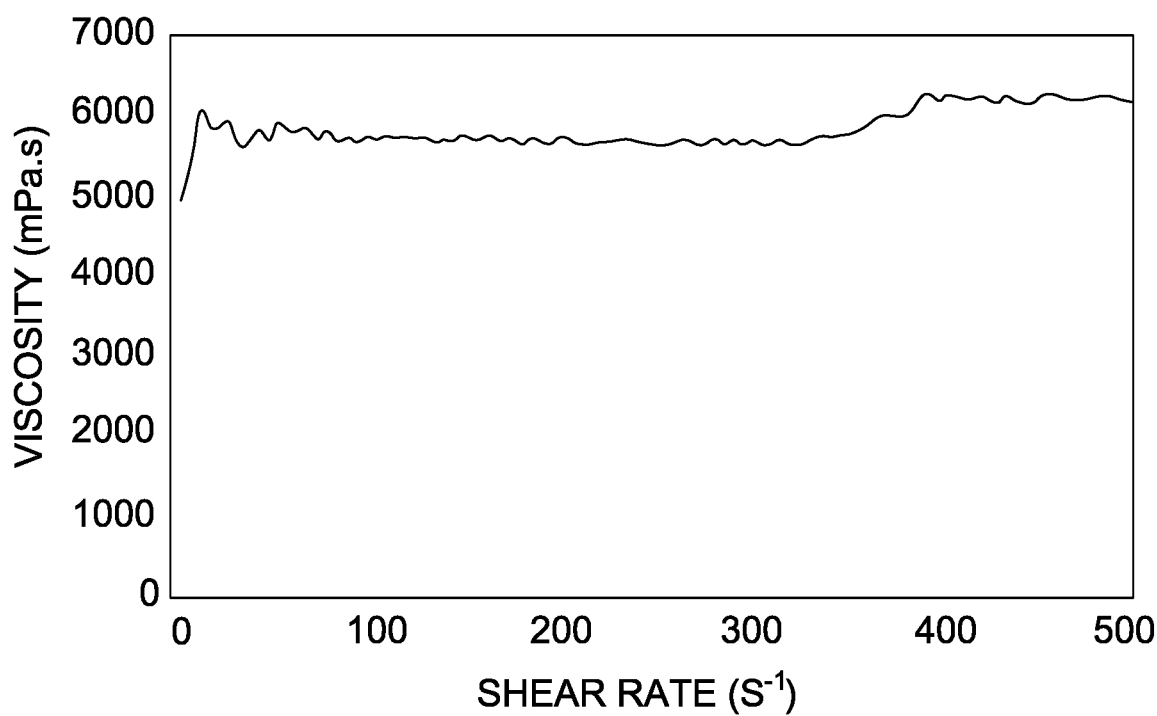
FIG. 24B depicts an exemplary embodiment of a viscosity curve for [OcGBOEt][DHDGA] in accordance with the present disclosure.

The viscosity of ionic liquids was determined using a Haake Mars rheometer with cone-plate measuring system (cone angle 1°). Two different tests were conducted to determine the viscosity of ionic liquids. First, the shear rate was increased from 0 to 500 s$^{-1}$ and the flow curve was obtained. Second, the shear rate ramped from 1 to 200 s$^{-1}$ with stepwise in which the shearing maintained 30 s for each shear rate. The viscosity of [OcGBOEt][DHDGA] was 5.85 Pa·s, which was 2.2 times greater than the viscosity of [A336][DHDGA] which was found to be 2.68 Pa·s. (see FIGS. 24A-B).

Results and Discussion

Synergistic Effect of Cationic-Anionic Components of Functionalized ILs

Figure 2A:
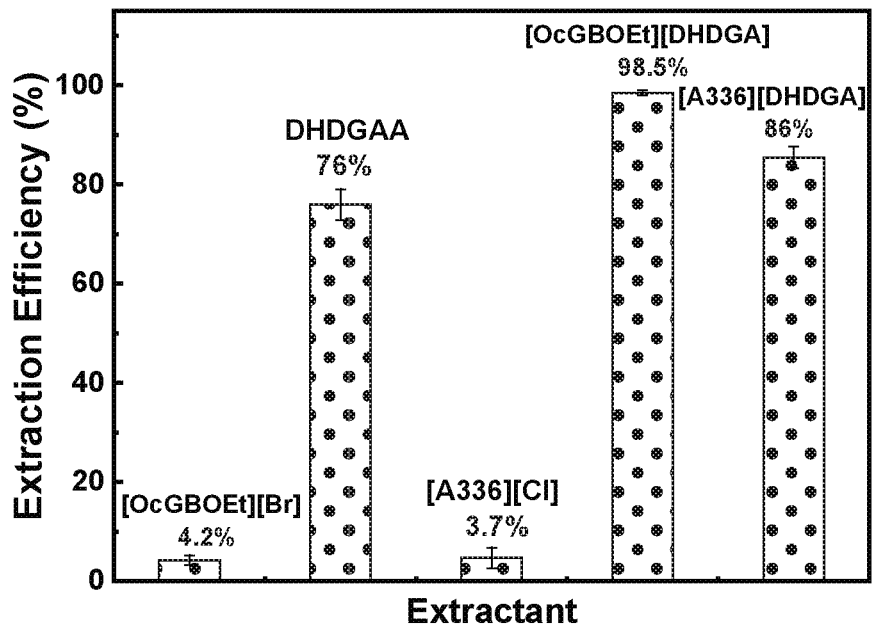
FIG. 2A depicts an exemplary embodiment of a comparison of the extraction performance of FILs in accordance with the present disclosure compared to their precursors for Extraction efficiency (% E) (pH=4, time=90 min, temperature: =33 OC, [$Eu^{3+}$]=0.001 M, [extractant]=0.04 M, diluent=chloroform).

To investigate the synergistic effect of both the cationic and anionic components of the synthesized functional ionic liquids (FILs) on the extractability performance, extraction efficiency of $Eu^{3+}$ from nitrate solution using [OcGBOEt][DHDGA] and [A336][DHDGA] was examined and compared to their precursors. As shown in FIG. 2A, the extraction efficiencies of [OcGBOEt], [A336], and [DHDGA] were 4.2%, 3.7%, and 76%, respectively compared to 98.5% and 86% for [OcGBOEt][DHDGA] and [A336][DHDGA], respectively.

Figure 2B:
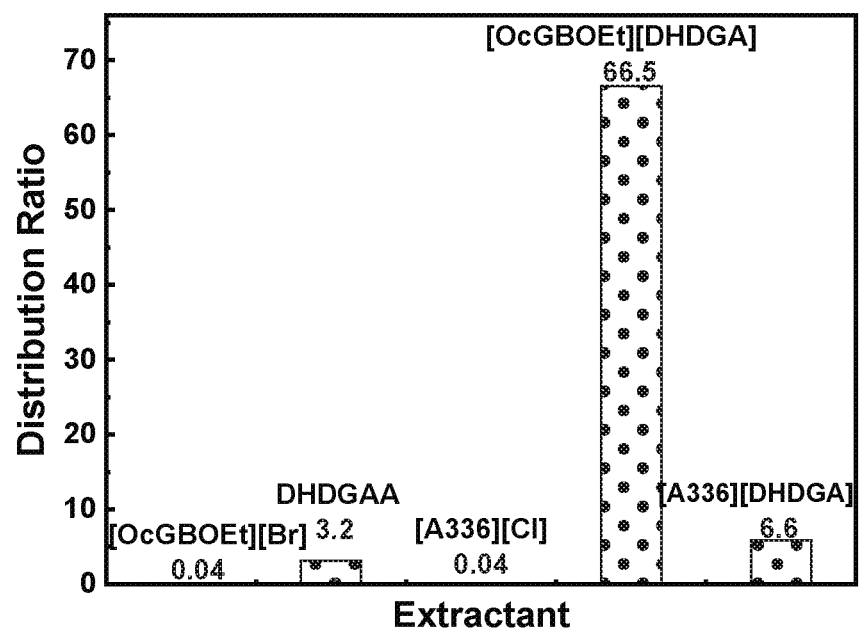
FIG. 2B depicts an exemplary embodiment of a comparison of the extraction performance of FILs in accordance with the present disclosure compared to their precursors for Distribution coefficient (D) (pH=4, time=90 min, temperature: =33 OC, [$Eu^{3+}$]=0.001 M. [extractant]=0.04 M, diluent=chloroform).

FIG. 2B shows the distribution coefficients of $Eu^{3+}$ in the two functionalized IL and in their anionic and cationic precursors. As indicated, the D value of $Eu^{3+}$ reached as high as 45 and 6.6 in [OcGBOEt][DHDGA] and [A336][DHDGA], respectively. This enhanced extraction by the two functionalized ILs is due to the inner synergistic effect of both the acidic and basic components. Both the cation and the anion involve in the extraction process and in some embodiments form coordination bonds with $REE^{3+}$ which would help to increase the capacity of IL-system and reduce the loss of cation and anion to the aqueous phase.

Influence of Solution Acidity

Figure 3:
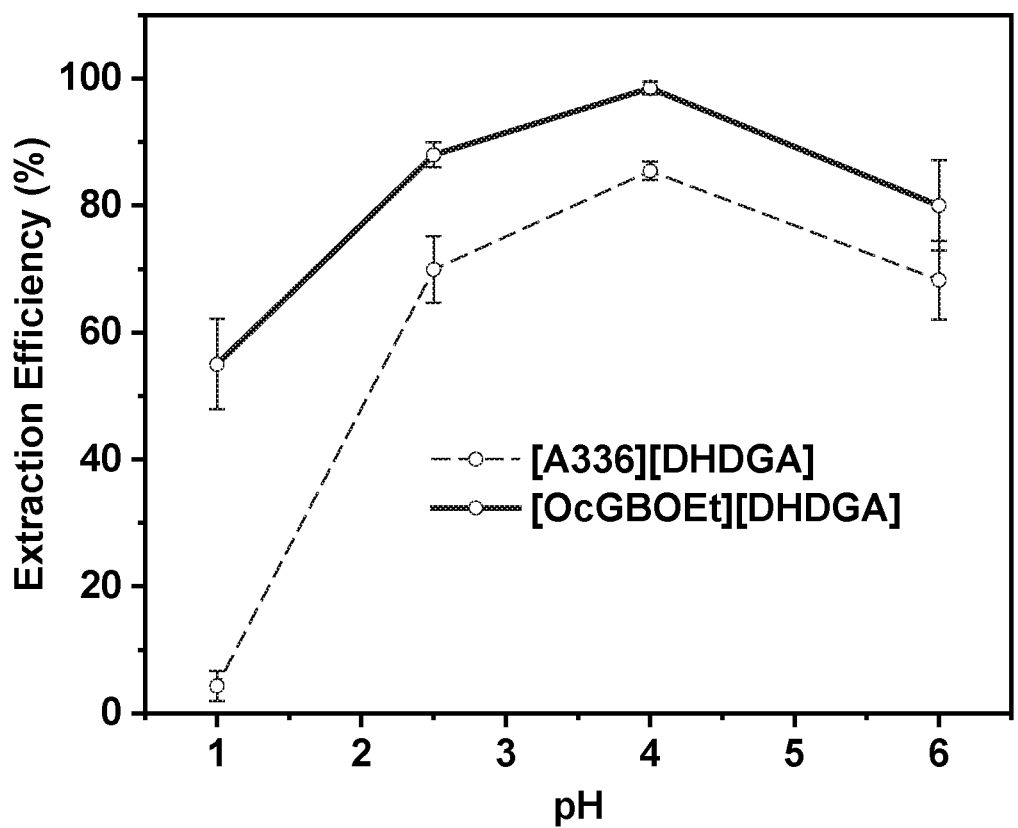
FIG. 3 depicts an exemplary embodiment of the effect of the acidity of aqueous phase (pH) on the extraction efficiency of $Eu^{3+}$ in accordance with the present disclosure ([OcGBOEt][DHDGA]=[A336][DHDGA]=0.04 $molL^{-1}$, $Eu^{3+}$=0.001 $molL^{-1}$, time=90 min. temperature=33° C.).

To investigate the effect of solution acidity on the extraction behavior of the functionalized ionic liquids, the recoveries of europium ions ($Eu^{3+}$) extracted using [OcGBOEt][DHDGA] and [A336][DHDGA] were determined at different pH values of 1, 2.5, 4 and 6. As seen in FIG. 3, the extraction efficiency of $Eu^3$ decreased as the acidity of the aqueous phase increased. Extraction efficiency (% E) at pH 1 was about 55% and 4.3% for [OcGBOEt][DHDGA] and [A336][DHDGA], respectively, and increased to 98.5% and 85.7% at pH 4. This indicated that high acidity has a negative impact on the extraction efficiency of FILs. As shown, % E values displayed a slow increase in the pH range of 2.5-4, however at pH >4, the extraction efficiency dropped to 70-80%. Accordingly, in some embodiments of the present disclosure, the solution acidity has a pH of between about 2 to about 5, between about 2.5 to about 4.5, or about 4.

By comparing the % E values of [OcGBOEt][DHDGA] and [A336][DHDGA] at different solution acidities, it is clear that the extractability of [OcGBOEt][DHDGA] is much better than that of [A336][DHDGA] at high and medium pH values. These results therefore indicate that the [OcGBOEt] cations are more likely to form complexes with metal ions than the [A336] anion.

Figure 4:
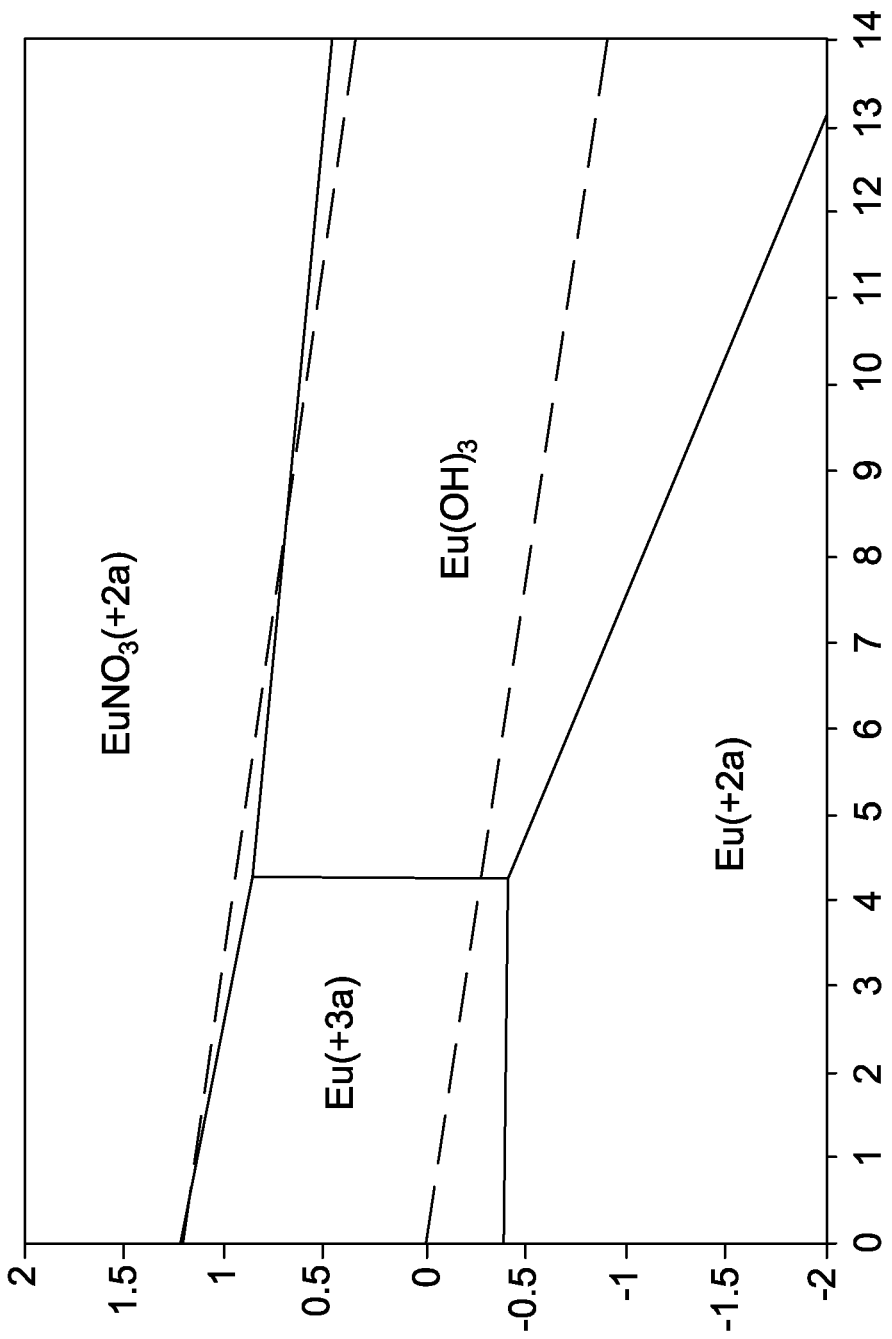
FIG. 4 depicts an exemplary embodiment of an Eh-pH diagram of europium species in nitric acid medium in accordance with the present disclosure (temperature=33° C., [$Eu^{3+}$]=0.001 M).

The pH dependency of the extraction process is explained by the competition between H and $Eu^{3+}$ ions on the ligand. Extraction of $H^+$ ions leads to a decrease in the effective ligand concentration in the organic phase, thereby decreasing extraction efficiency. The decrease in the extraction efficiency at pH 6 may be due to the hydrolysis of $Eu^{3+}$ and formation of $Eu(OH)_3$ species. The Eh-pH diagram Eu—$NO_3$—$H_2O$ system at 33° C. is shown in FIG. 4. This diagram helps to identify the nature and the stability of each species by determining the domain of un-complexed and hydrolytic species of rare earth ions. As shown, the hydrolysis of $Eu^{3+}$ is not significant until the pH value is greater than 4.5. As it is evident, the formation and precipitation of $Eu(OH)_3$ is the major factor affecting the solubility of europium ion under low acidic and alkaline conditions. In some embodiments, changing the temperature, europium concentration, and considering the other ions present in the solution change the domains and forms of different species.

Influence of REE Concentration

Extraction efficiency of europium was investigated using different initial concentrations of $Eu^{3+}$ ions in feed solution. The concentrations studied ranged from 0.5 to 10 mM of $Eu^{3+}$. The concentration of ILs in all the tests performed in these tasks was kept at 0.04 M in chloroform.

Figure 5A:
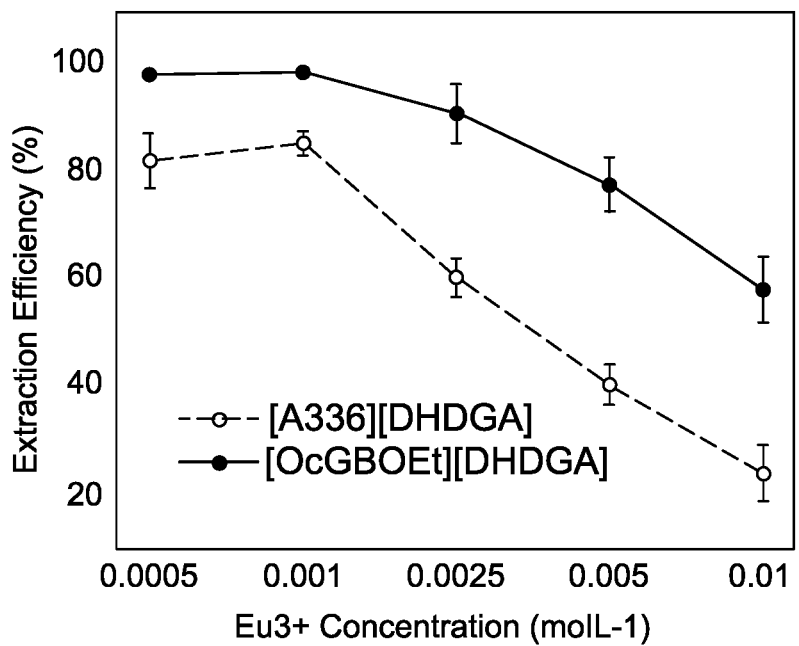
FIG. 5A depicts an exemplary embodiment of the influence of the initial $Eu^{3+}$ concentration on % E of $Eu^{3+}$ in accordance with the present disclosure.

As shown in FIG. 5A, in the case of [OcGBOEt][DHDGA], the extraction percentage remains constant (~98%) as a function of europium ion concentration between 0.5 and 5 mM. At low $Eu^{3+}$ concentrations, the ionic liquid is present in a large excess, and loading of the ionic liquid phase does not influence the distribution of $Eu^{3+}$. At higher $Eu^{3+}$ concentrations, the ionic liquid was no longer in excess and the extraction equilibrium was shifted due to the loading effects.

Figure 5B:
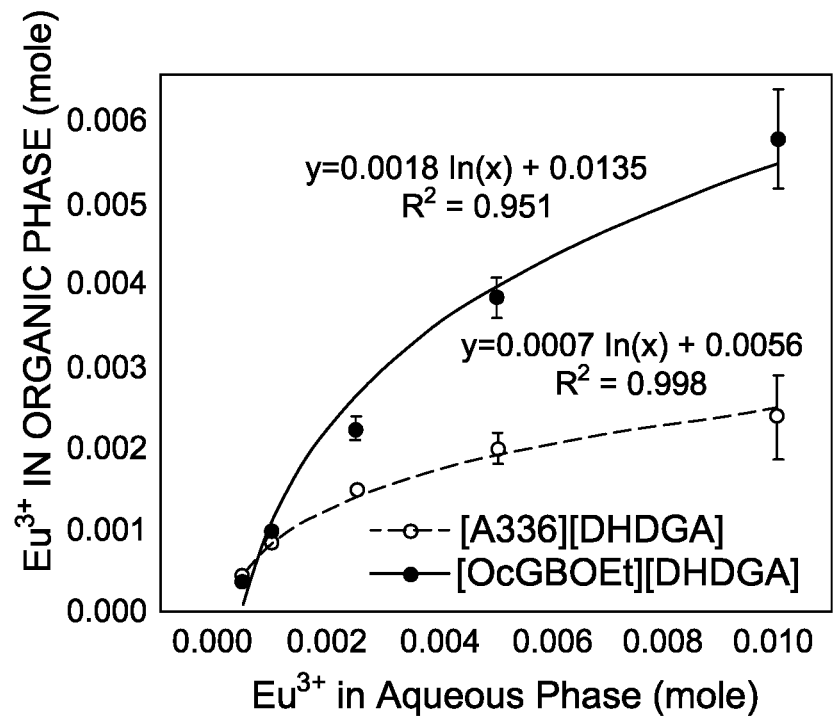
FIG. 5B depicts an exemplary embodiment of the loading capacity of the synthesized FILs in accordance with the present disclosure (O/A=1; time=90 min; temperature=32° C.; pH=4; [IL]=0.04 $molL^{-1}$).

In the case of [A336][DHDGA], at an initial $Eu^{3+}$ concentration of 0.5 mM in the aqueous phase, around 80% of the $Eu^{3+}$ ions were extracted. However, the maximum amount of $Eu^{3+}$ extracted by [A336][DHDGA] was observed at 1 mM (% E of about 85%). With increasing the initial concentration to more than 1 mM, the extraction efficiency drops sharply due to the decrease in the loading capacity of [A336][DHDGA]. In FIG. 5B, the loading capacities of 0.04 M FILs are presented. It was found that the concentration of $Eu^{3+}$ in the organic phase increased with increasing concentration of $Eu^{3+}$ in the aqueous phase. As is evident, the loading capacity of [OcGBOEt][DHDGA] was about three times higher than the loading capacity of [A336][DHDGA].

Influence of Diluent Type

Figure 6:
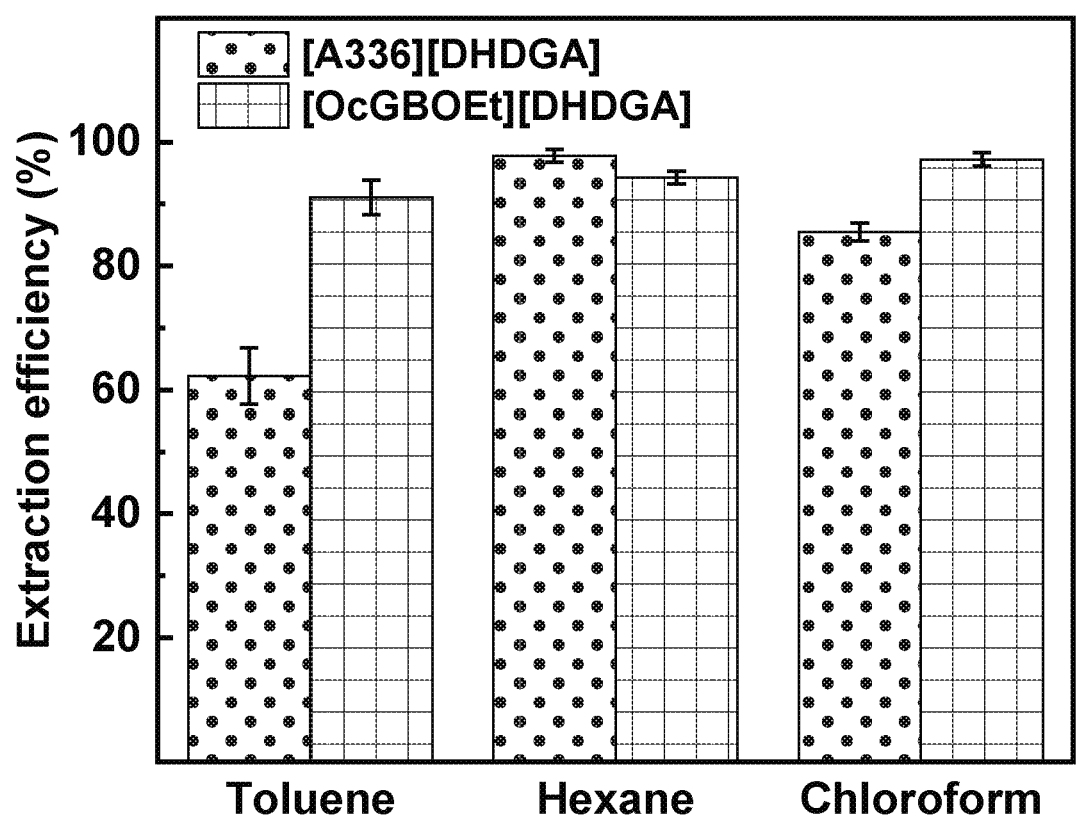
FIG. 6 depicts an exemplary embodiment of the influence of diluent type on the extraction efficiency in accordance with the present disclosure (% E) of $Eu^{3+}$ (time=90 min; temperature=33° C.; pH=4; [IL]=0.04 M).

The effect of diluent type on the extraction of europium ions from aqueous nitrate feed solution by the synthesized ILs was also investigated. Three diluents were used: hexane, toluene, and chloroform. Both [OcGBOEt][DHDGA] and [A336][DHDGA] were well miscible in all diluents. As results indicated (FIG. 6), lower values of % E were obtained with toluene (dielectric constant of about 2.3). It is also observed that [OcGBOEt][DHDGA] efficiently extracts $Eu^{3+}$ ions with all three types of diluents but the % E is a little bit higher with chloroform (dielectric constant of about 4.8). As shown in FIG. 6, the extraction efficiency of [A336][DHDGA] in hexane diluent (dielectric constant of about 1.9) is higher than that of [OcGBOEt][DHDGA]. In addition to the influence of dielectric constant, the interaction between the diluent and ILs could largely impact the extraction efficiency. A weaker interaction between extractant and diluent would result in a higher extraction capacity.

Extraction Stoichiometry

Figure 7:
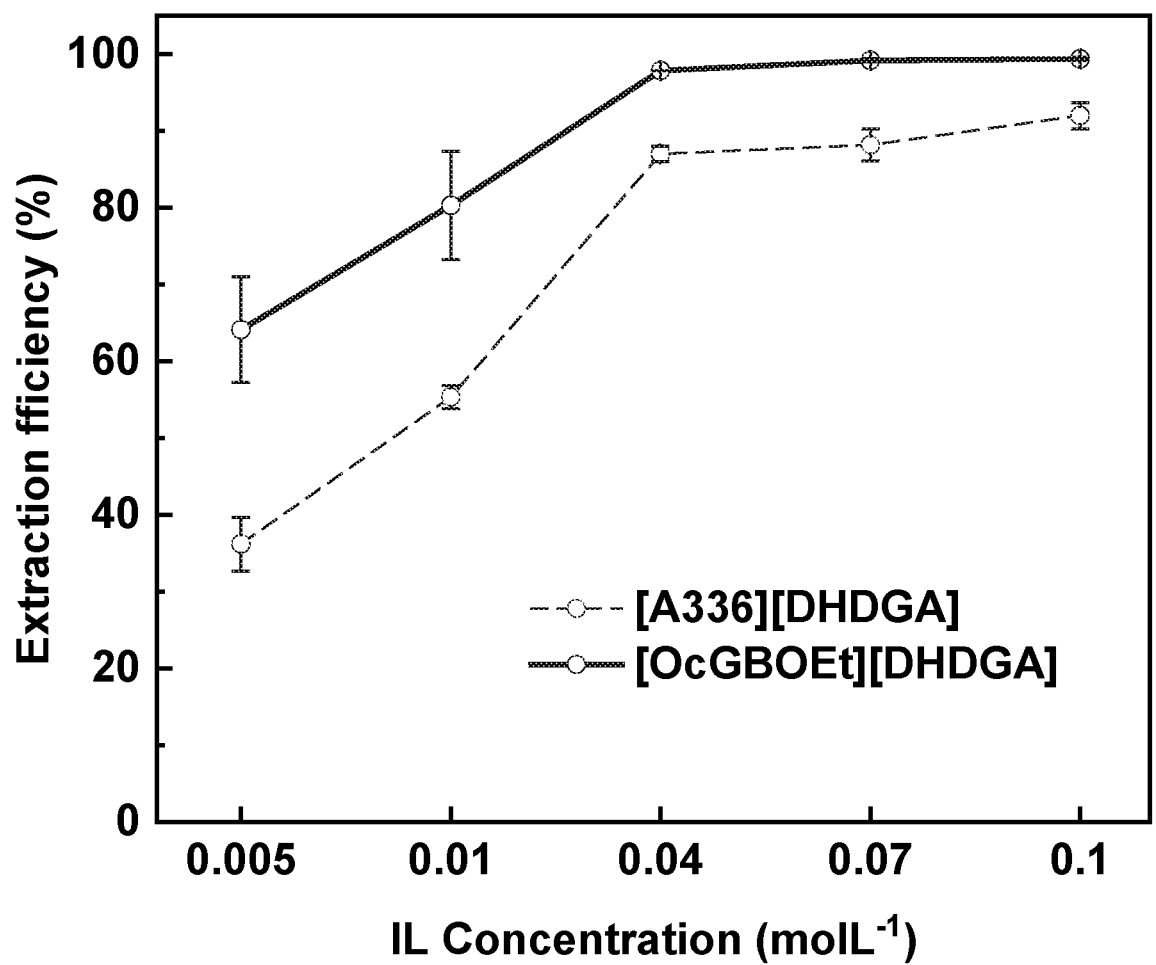
FIG. 7 depicts an exemplary embodiment of the effect of ionic liquid concentration on europium ion extraction in accordance with the present disclosure ([$Eu^{3+}$]=1 mM; time=90 minutes; temperature=33° C.; pH=4).

To understand the extraction mechanism, it was important to determine the number of a specific IL involved metal-ligand complexation. This was obtained by measuring the distribution ratio of europium as a function of IL concentration in organic phase and plotting the logarithmic value of the measured distribution ratio against concentration of ILs. The stoichiometry obtained by slope analysis is specific to the experimental conditions used in this study and changing the conditions could result in a different REE:FIL ratio. As shown in FIG. 7, the extraction percentage increased with the increase in concentration of FILs. In the case of [OcGBOEt][DHDGA], 0.04 M was enough to recover about 98% of the $Eu^{3+}$ ions, while the maximum recovery achieved by [A336][DHDGA] was 92% with 0.1 M ionic liquid. These results are in agreement with the results obtained when studying the effect of $Eu^{3+}$ concentration on the extraction efficiency of FILs. The results clearly indicated the higher loading capacity of [OcGBOEt][DHDGA].

Figure 8A:
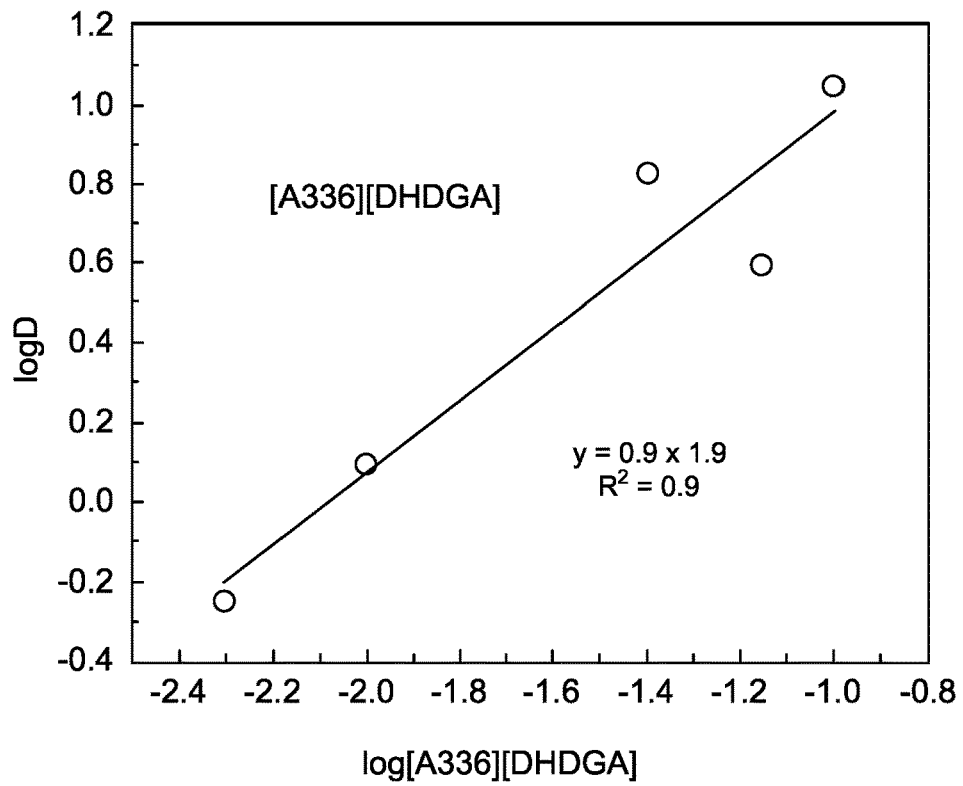
FIG. 8A depicts an exemplary embodiment of the linear relationship between log [D] and log[IL] in $Eu^{3+}$ extraction [OcGBOEt][DHDGA] in accordance with the present disclosure.
Figure 8B:
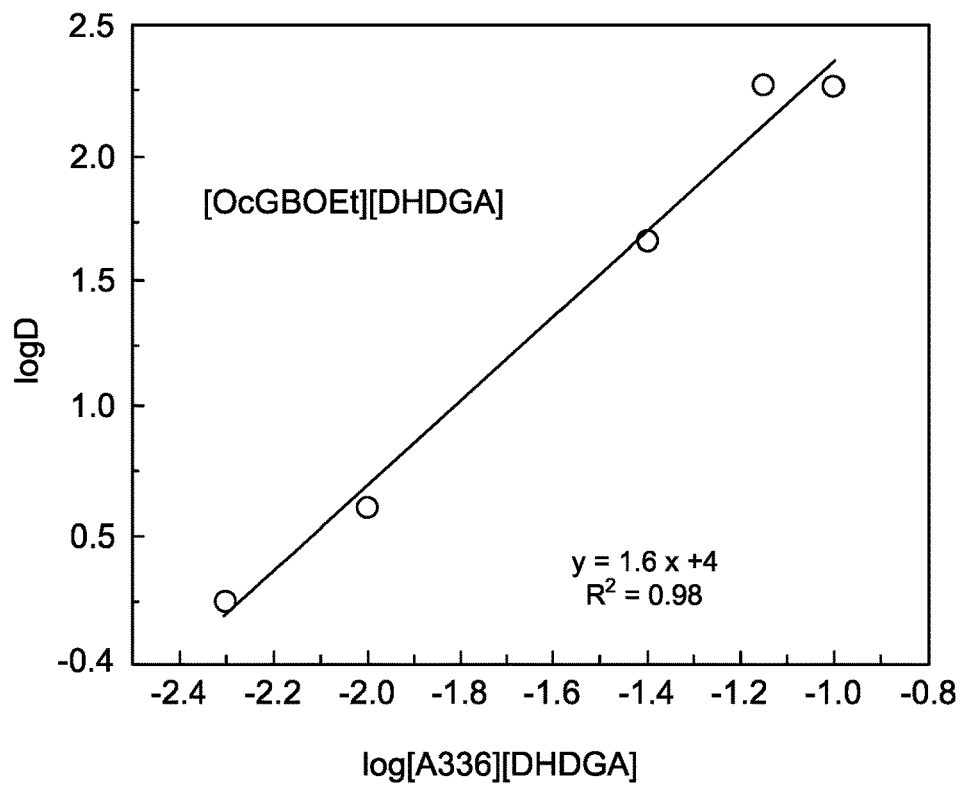
FIG. 8B depicts an exemplary embodiment of the linear relationship between log [D] and log[IL] in $Eu^{3+}$ extraction [A336][DHDGA] in accordance with the present disclosure.

As seen in FIGS. 8A-B, the linear relationship between the log D and log [IL] was obtained with a slope of 1.6 for [OcGBOEt][DHDGA] and 0.9 for [A336][DHDGA] in an IL concentration range of 0.0005-to-0.1 M. The complex stoichiometries were determined using slope analysis according to the following equation $$\log D = \log K_{ex} + n \log[IL] \qquad (5)$$

where D and $K_{ex}$ are distribution ratio and the extraction equilibrium constant.

Kinetic Studies

Figure 9:
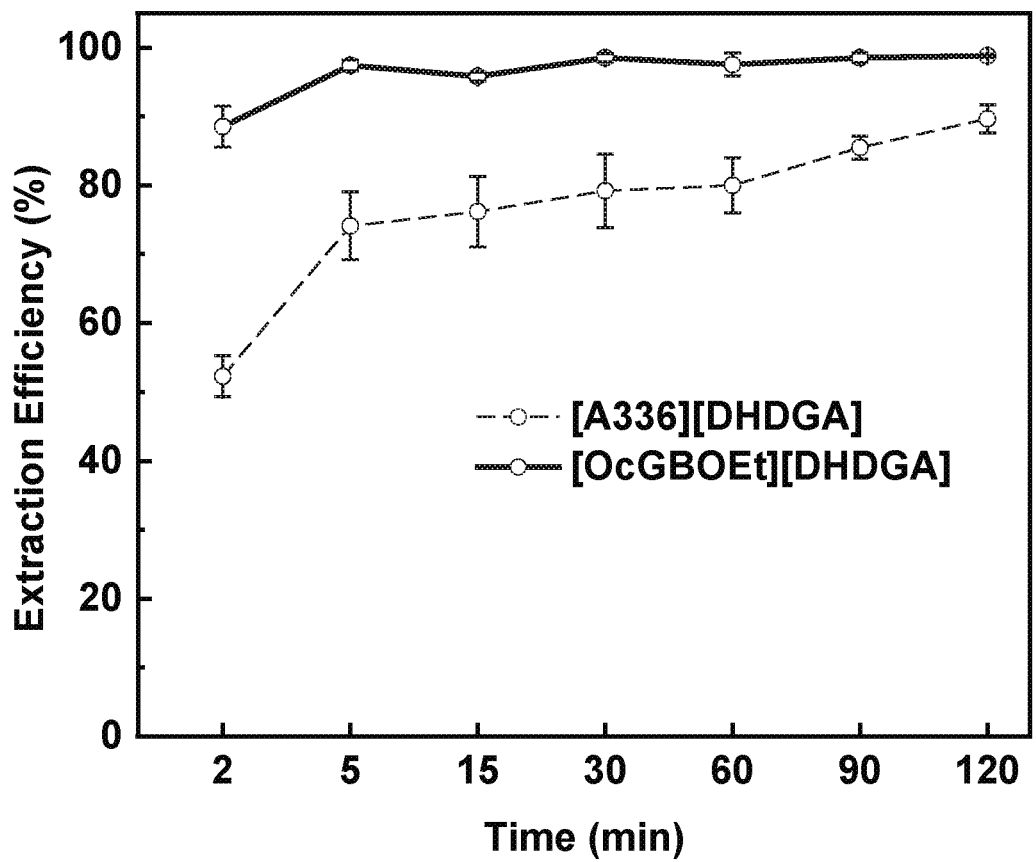
FIG. 9 depicts an exemplary embodiment of the effect of time on the extraction of $Eu^3$ in accordance with the present disclosure ([OcGBOEt][DHDGA]=[A336][DHDGA]=0.04 molL-1, [Eu$^{3+}$]=1 mM, pH=4, temperature=33° C.).

The extraction kinetics were evaluated based on the time of contact (extraction time) of aqueous phase containing europium with the ionic liquid phase (organic phase). The results indicated that the extraction kinetics were relatively fast. About 96% of europium ions were extracted in first 5 minutes using [OcGBOEt][DHDGA] while ~82% were extracted using [A336][DHDGA]. As is shown in FIG. 9, the extraction efficiency of [OcGBOEt][DHDGA] slightly increased to 97.4% when the extraction time increased to 5 minutes, and then reached a plateau (E % of about 98-100%) as time increased to 120 minutes. About 75% of $Eu^{3+}$ was extracted by [A336][DHDGA] in 5 minutes and increased to about 90% as the extraction time increased to 120 minutes. This is mainly important for processing radio toxic elements, such as f-block elements, which continuously emit particle radiation like alpha and beta, and electromagnetic radiation like gamma. The organic phase is exposed to such radiations, and the longer contact time leads to larger chances of radiolytic degradation.

Investigations on Extraction Thermodynamics

Figure 10:
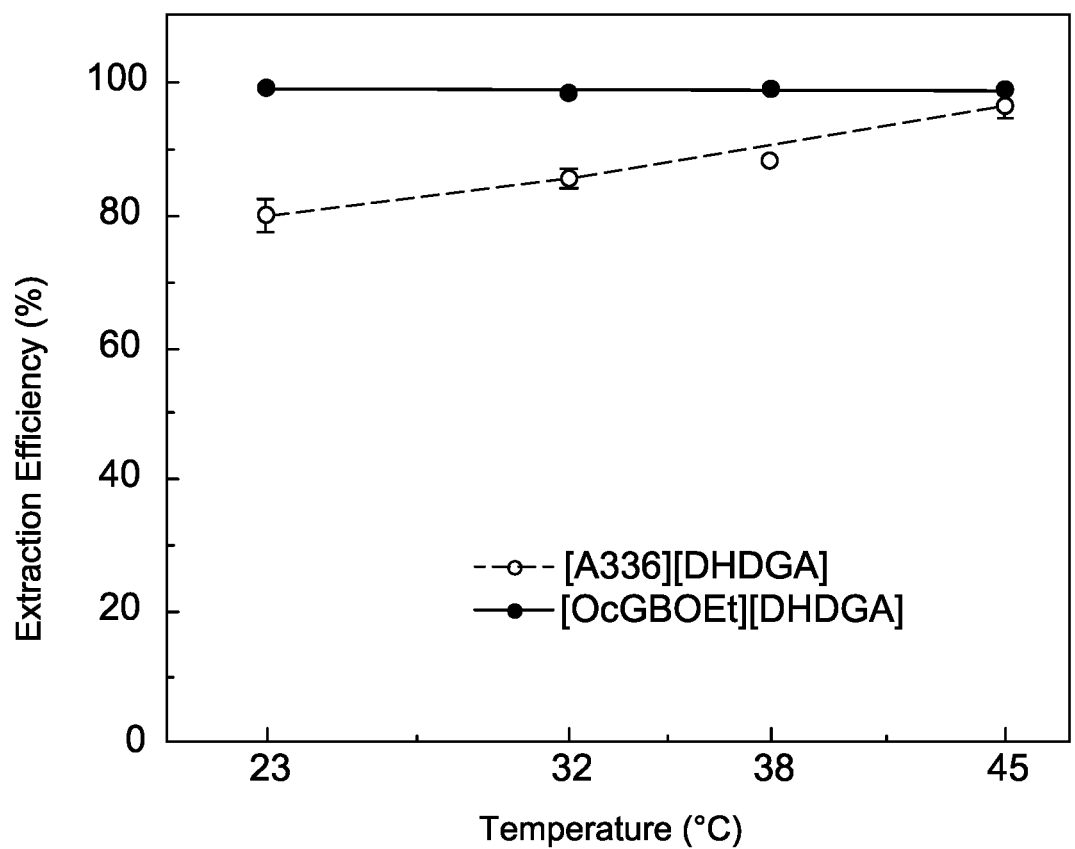
FIG. 10 depicts an exemplary embodiment of the effect of temperature on the extraction of Eu$^{3+}$ in accordance with the present disclosure ([IL]=0.04M, [Eu$^{3+}$]=1 mM, time=90 min; pH=4).

To calculate the key thermodynamic parameters of the extraction process of REEs by [OcGBOEt][DHDGA] and [A336][DHDGA], extraction experiments of $Eu^{3+}$ were carried out over a temperature range of 23-47° C. As shown in FIG. 10, temperature did not have a significant effect on the extraction efficiency of [OcGBOEt][DHDGA] as the extraction process was highly efficient at room temperature. However, it is evident that an increase in temperature from 23° C. to 47° C. lead to an increase in % E of [A336][DHDGA] from 79.8% to 96.4%, respectively.

According to the Van't Hoff equation, enthalpy change of the reaction ($\Delta H°$) can be obtained by the following equation:

$$\log D = -\frac{\Delta H}{2.303R}\frac{1}{T} + C \quad (6)$$

where R is the gas constant and C is the integration constant.

Figure 11:
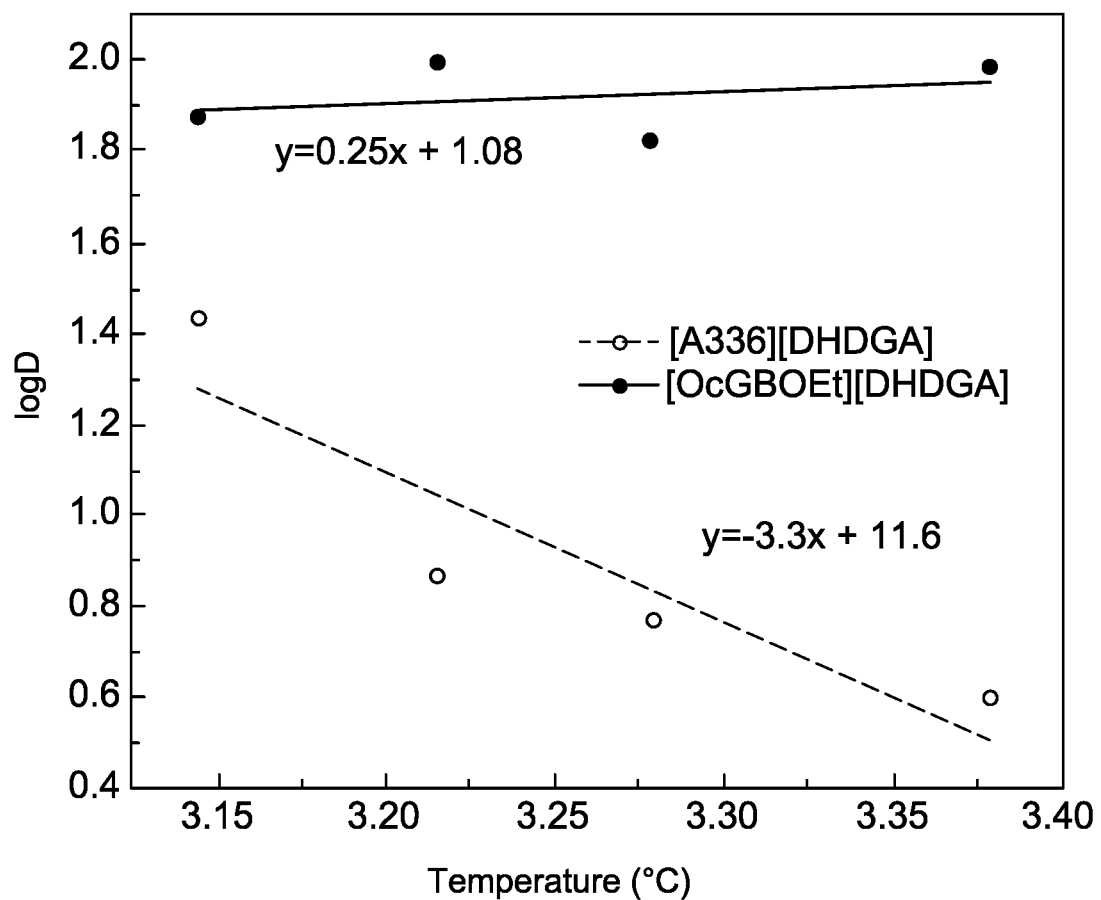
FIG. 11 depicts an exemplary embodiment of a Van't Hoff plot correlating a distribution coefficient (D) with the extraction temperature (T) in accordance with the present disclosure ([IL]=0.04 M, [Eu$^{3+}$]=1 mM, time=90 min; pH=4).

As shown in FIG. 11, plotting log D versus 1000/T resulted in a straight line with a slope of 0.25 and −3.3 for [OcGBOEt][DHDGA] and [A336][DHDGA], respectively. As presented in Table 2, the $\Delta H$ value for [A336][DHDGA] was positive which means that the extraction of europium ions was endothermic. The $\Delta H$ value for [OcGBOEt][DHDGA] was negative showing the exothermic nature of the extraction by [OcGBOEt][DHDGA].

The change in Gibbs free energy ($\Delta G°$) was calculated using the equation (7):

$$\Delta G = -RT \ln K_{ex} \quad (7)$$

$K_{ex}$ is the extraction equilibrium constant and can be calculated using equation 5 and from the intercept of the plot of log D versus log[IL] (FIGS. 8A-B). The change in entropy ($\Delta S°$) at a particular temperature can be calculated using following equation:

$$\Delta S = \frac{\Delta H - \Delta G}{T} \quad (8)$$

TABLE 2

Thermodynamic parameters of $Eu^{3+}$ extractions in nitric acid medium (temperature = 33° C.; time = 90 min.; pH = 4).

| [A336][DHDGA] | | | [OcGBOEt][DHDGA] | | |
|---|---|---|---|---|---|
| ΔH | ΔG | ΔS | ΔH | ΔG | ΔS |
| 63.2 | −10.8 | 248.3 | −4.8 | −22.8 | 59.2 |

The positive values of $\Delta S°$ suggest that the degree of disorder increased upon the $Eu^{3+}$ extraction. The negative values of Gibbs free energy indicated that the extraction process is feasible. As presented in Table 2, the extraction by [OcGBOEt][DHDGA] was more favorable than the extraction by [A336][DHDGA].

Studies on the Extraction Selectivity

Light and Heavy REEs

Figure 12:
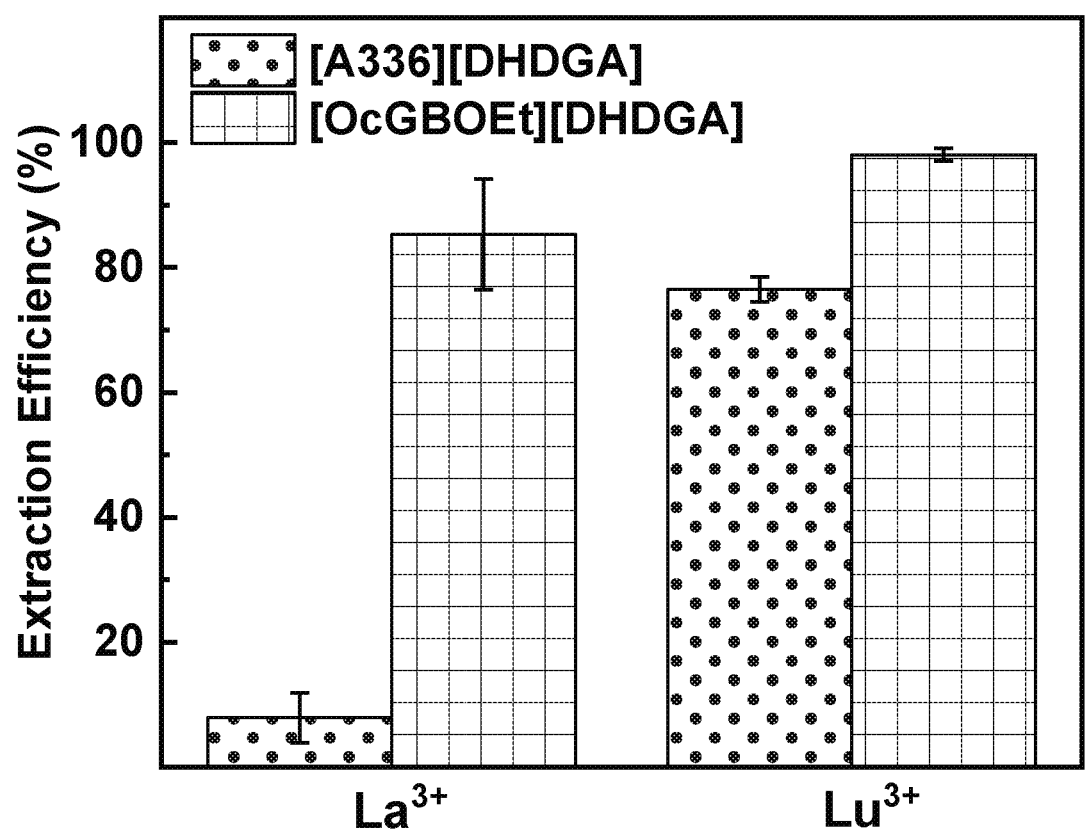
FIG. 12 depicts an exemplary embodiment of the affinity of synthesized ILs to light and heavy REEs in accordance with the present disclosure ([REE]=1 mM; time=90 min; temperature=33° C.; pH=4; [IL]=0.04 M).

Extraction of $La^{3+}$ and $Lu^{3+}$, as representatives of light and heavy REEs, using [OcGBOEt][DHDGA] and [A336][DHDGA] was studied separately to find out the affinity of the synthesized ILs to heavy and light REEs. As it is shown in FIG. 12, [A336][DHDGA] obviously had much more affinity to heavy REEs, while [OcGBOEt][DHDGA] was less selective.

Rare Earth Mixtures

Figure 13:
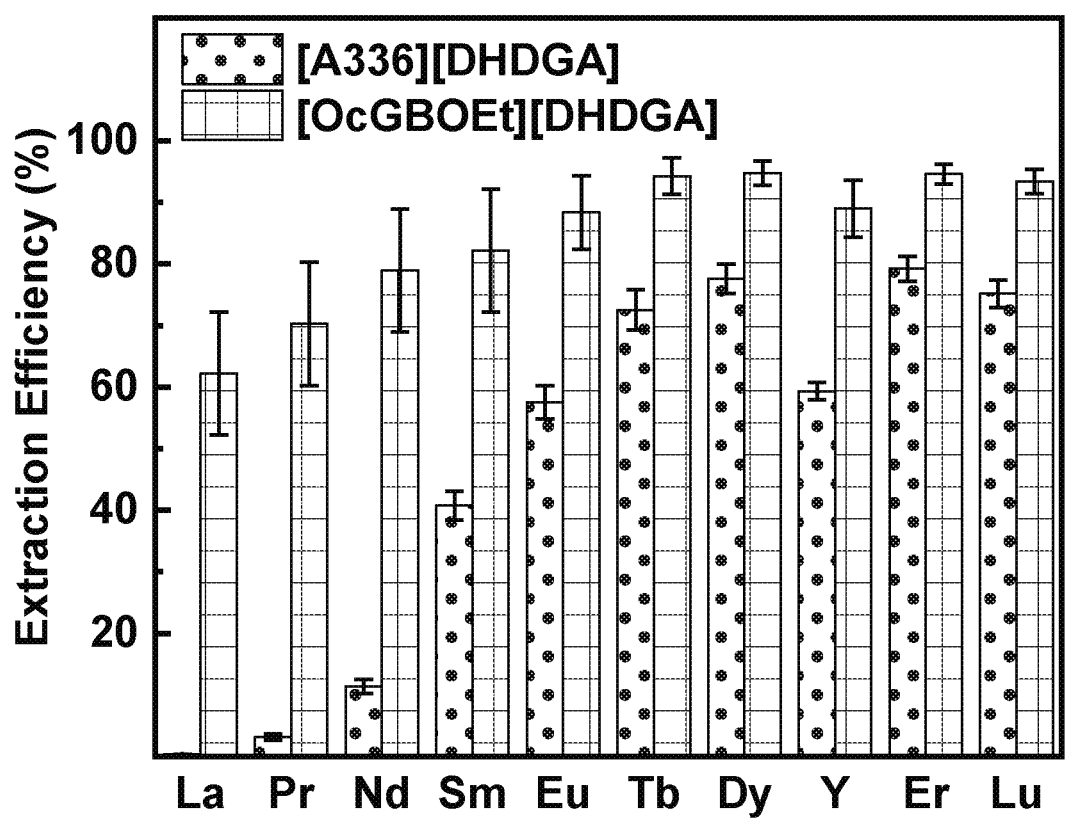
FIG. 13 depicts an exemplary embodiment of extraction efficiencies (% E) of rare earth ions from nitrate aqueous solution in accordance with the present disclosure ([REE] =100 mg/l; temperature=33° C.; time=90 min; pH=4).

A competitive extraction of ten rare earth elements using [OcGBOEt][DHDGA] and [A336][DHDGA] was carried out to assess the separation efficiency and the selectivity of the proposed IL system. The extraction efficiencies are plotted in FIG. 13. The [OcGBOEt][DHDGA] effectively extracts all REEs, however, it showed more affinity for middle and heavy REEs. On the other hand. [A336][DHDGA] had a higher selectivity for heavy rare earth elements. The distribution ratios and the separation factors calculated using Eq. 2 & 4, are tabulated in Tables 3 & 4, respectively. As indicated, the separation efficiency of [A336][DHDGA] was much higher than that of [OcGBOEt][DHDGA]. As shown in FIG. 13 and Tables 3 & 4, it is evident that $La^{3+}$, $Pr^{3+}$ and to a smaller extent $Nd^3$, were much less efficiently extracted than the middle and heavy rare elements. This suggests that [A336][DHDGA] is used to separate light rare earth elements from the heavier ones. Yttrium is behaving like heavy REEs in nitrate media but the extraction percentage was clearly less than the adjacent heavy REEs with closer ionic size.

The separation experiments were conducted using 0.07 M of FILs, however, lower concentration of FILs (0.04 M) was also examined to observe potential changes in separation efficiency. The results showed a small change in the selectivity of [A336][DHDGA] but an increase in the selectivity of [OcGBOEt][DHDGA] towards heavier rare earth elements.

TABLE 3

Separation factors (SF) of REEs in [OcGBOEt][DHDGA] + Chloroform system.

|    | Pr | Nd | Sm | Eu | Tb | Dy | Y | Er | Lu |
|----|-----|-----|-----|------|------|------|-----|------|------|
| La | 2.2 | 1.9 | 2.4 | 6.95 | 15.1 | 16.6 | 7.4 | 16.0 | 12.9 |
| Pr |     | 0.8 | 1.1 | 3.2  | 6.9  | 7.7  | 3.4 | 7.4  | 5.9  |
| Nd |     |     | 1.2 | 3.6  | 7.8  | 8.5  | 3.8 | 8.2  | 6.7  |
| Sm |     |     |     | 2.9  | 6.4  | 7.0  | 3.1 | 6.8  | 5.5  |
| Eu |     |     |     |      | 2.2  | 2.4  | 1.1 | 2.3  | 1.9  |
| Tb |     |     |     |      |      | 1.1  | 0.5 | 1.1  | 0.9  |
| Dy |     |     |     |      |      |      | 0.4 | 0.9  | 0.8  |

TABLE 3-continued

Separation factors (SF) of REEs in [OcGBOEt][DHDGA] + Chloroform system.

| | Pr | Nd | Sm | Eu | Tb | Dy | Y | Er | Lu |
|---|---|---|---|---|---|---|---|---|---|
| Y | | | | | | | | 2.2 | 1.7 |
| Er | | | | | | | | | 0.8 |

TABLE 4

Separation factors (SF) of REEs in [A336][DHDGA] + Chloroform system.

| | Pr | Nd | Sm | Eu | Tb | Dy | Y | Er | Lu |
|---|---|---|---|---|---|---|---|---|---|
| La | 10.8 | 42.6 | 228.5 | 450.4 | 877.5 | 1149.3 | 484.6 | 1266.2 | 1006.6 |
| Pr | | 3.9 | 21.1 | 41.5 | 80.9 | 105.9 | 44.7 | 116.8 | 92.8 |
| Nd | | | 5.4 | 10.6 | 20.6 | 27.0 | 11.4 | 29.7 | 23.7 |
| Sm | | | | 1.9 | 3.8 | 5.0 | 2.1 | 5.5 | 4.4 |
| Eu | | | | | 1.9 | 2.6 | 1.1 | 2.8 | 2.2 |
| Tb | | | | | | 1.3 | 0.6 | 1.4 | 1.1 |
| Dy | | | | | | | 0.4 | 1.1 | 0.9 |
| Y | | | | | | | | 2.6 | 2.0 |
| Er | | | | | | | | | 0.8 |

Back-Extraction Studies

Figure 14:
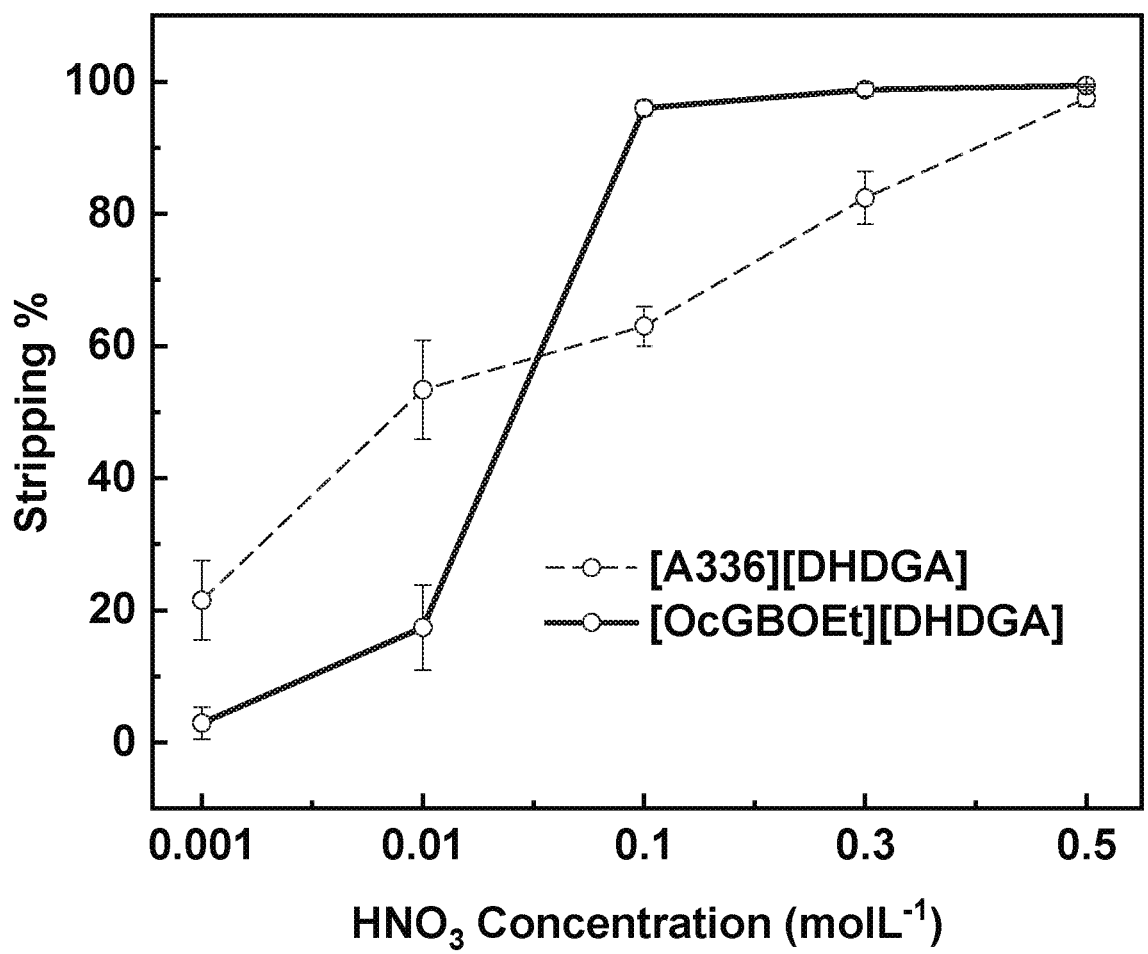
FIG. 14 depicts an exemplary embodiment of the stripping of loaded [OcGBOEt][DHDGA] and [A336][DHDGA] with different concentrations of nitric acid in accordance with the present disclosure.

Back-extraction (also known as stripping) studies are important for evaluating the suitability of an extractant for industrial operations. One of the challenges facing the industrial implementation of ionic liquids as extractants is the feasibility of stripping of metal ion from the ionic liquid phase. In some cases, since the extraction of metal ion by ILs may not be very sensitive to pH, stripping the loaded phase by adjusting the pH may not work efficiently. To overcome this problem, some aqueous soluble complexing agents are usually used to facilitate stripping. In the present investigation, nitric acid solutions with different concentrations were used without any complexing agent to examine the back-extraction feasibility. The results (FIG. 14) showed that the stripping amount of [OcGBOEt][DHDGA] was very high at nitric acid concentrations above 0.1 M (pH<1). Approximately 95, 99.7, and 100% of the europium ions were extracted using 0.1, 0.3 and 0.5 M nitric acid. As shown in FIG. 14, the amount of europium stripped off [OcGBOEt][DHDGA] by 0.001 and 0.01 M nitric acid was not significant, while about 20% and 53% of europium was stripped off [A336][DHDGA] with 0.001 and 0.01 M $HNO_3$, respectively. The stripping efficiency increased to 66, 83, and 100% for [A336][DHDGA] using 0.1, 0.3, and 0.5 M nitric acid.

The stability and reusability of functional ionic liquids are essential from a practical point of view. The reusability of [A336][DHDGA] and [OcGBOEt][DHDGA] was studied by stripping loaded FILs with 0.3 and 0.1 M nitric acid, respectively, and then re-loading with 0.001 M $Eu^{3+}$ aqueous feed. The extraction was performed at pH 4 and 32° C. for 90 minutes. The results indicated that the extractability of both ionic liquids after being stripped remained as high as the extractability of fresh FILs. The extraction efficiencies of stripped 0.04 M of [A336][DHDGA] and [OcGBOEt][DHDGA] were ~86% and 95%, respectively.

Results

Described herein, two novel ammonium-based functional ionic liquids (FILs): trioctyl(2 ethoxy-2-oxoethyl) ammonium dihexyl diglycolamate, [OcGBOEt][DHDGA], and trioctylmethyl ammonium dihexyl diglycolamate, [A336][DHDGA] were synthesized and tested, for the first time, for the recovery and separation of europium and other rare earth elements from nitric acid solutions. The following statements are concluded:

Both functionalized ionic liquids showed superior extraction performance for $Eu^{3+}$ as compared to their precursors. The extraction efficiencies of [OcGBOEt][DHDGA] and [A336][DHDGA] were 97.8% and 87%, respectively as compared to 4.2%, 3.7%, and 76% for [OcGBOEt][Br], [A336][Cl], and DHDGAA, respectively.

Highest extraction of $Eu^{3+}$ ions by both [OcGBOEt][DHDGA] and [A336][DHDGA] occurred around pH 4.

Kinetic studies showed that the extraction process was relatively fast with 97% of europium ions extracted in first 5 minutes using [OcGBOEt][DHDGA] compared to ~75% extracted using [A336][DHDGA].

Results showed that temperature had a significant effect on the extraction efficiency of $Eu^{3+}$ when [A336][DHDGA] was used, increasing the temperature from 23° C. to 47° C. lead to an increase in the extraction efficiency of $Eu^{3+}$ from 80% to 96%, respectively.

Extraction efficiency of $Eu^{3+}$ ions using [A336][DHDGA] was increased by using hexane as solvent.

A linear regression analysis of the plot of log D as a function of log [IL] indicated the formation of the 1:1 metal-ligand complex for [A336][DHDGA], but higher metal uptake for [OcGBOEt][DHDGA].

Competitive extraction studies on ten rare earth elements indicated that the extractability of [OcGBOEt][DHDGA] was higher than that of [A336][DHDGA] while [A336][DHDGA] showed greater selectivity. Results also showed that both FILs have more affinity to the middle and heavy rare earth elements; and, further, back-extraction studies showed that [OcGBOEt][DHDGA] had better stripping properties compared to [A336][DHDGA]. Re-loading the stripped FILs showed that both FILs could be effectively reused for extraction of rare earth elements.

Results showed that alkane-based solvents, such as hexane, effectively worked as diluents for the synthesized ionic liquids.

What is claimed is:

1. A method of recovering rare earth elements, the method comprising:
   mixing an aqueous solution comprising a rare earth element with a non-aqueous solution comprising a functionalized ionic liquid, wherein the functionalized ionic liquid comprises a cationic component and an anionic component, and further wherein the cationic component and the anionic component of the functionalized ionic liquid each individually comprise an oxygen donating group;
   solvating the rare earth element with the functionalized ionic liquid;
   separating a non-aqueous phase comprising the rare earth element from the mixture; and
   recovering the rare earth element.

2. The method of claim 1, wherein the cationic component is selected from the group consisting of tricaprylmethyl ammonium, trioctyl(2-ethoxy-2-oxoethyl)ammonium, tributylmethyl ammonium, tributyl(2-ethoxy-2-oxoethyl) ammonium, and combinations thereof.

3. The method of claim 1, wherein the anionic component is selected from the group consisting of dihexyl diglycolamate, dioctyl diglycolamate, dibutyl diglycolamate and combinations thereof.

4. The method of claim 1, wherein the functionalized ionic liquid is selected from the group consisting of trioctyl (2-ethoxy-2-oxoethyl)ammonium dihexyl diglycolamate, tricaprylmethylammonium dihexyl diglycolamate, and combinations thereof.

5. The method of claim 1, wherein the rare earth element is selected from the group consisting of light rare earth elements, medium rare earth elements, heavy rare earth elements, and combinations thereof.

6. The method of claim 1, wherein the rare earth element is selected from the group consisting of dysprosium, cerium, praseodymium, neodymium, promethium, samarium, europium, gadolinium, terbium, holmium, erbium, thulium, ytterbium, lutetium, scandium, yttrium, and lanthanum, and combinations thereof.

* * * * *